US011013208B2

(12) United States Patent
Kerrigan et al.

(10) Patent No.: US 11,013,208 B2
(45) Date of Patent: *May 25, 2021

(54) HYBRID BW-TYPE MUSHROOM STRAINS AND LINES AND METHODS AND USES THEREFOR

(71) Applicant: Sylvan America, Inc., Kittanning, PA (US)

(72) Inventors: Richard Kerrigan, Kittanning, PA (US); Mark Wach, Allison Park, PA (US); Michelle Schultz, New Bethlehem, PA (US)

(73) Assignee: SYLVAN AMERICA, INC., Kittanning, PA (US)

( * ) Notice: Subject to any disclaimer, the term of this patent is extended or adjusted under 35 U.S.C. 154(b) by 337 days.

This patent is subject to a terminal disclaimer.

(21) Appl. No.: 15/109,913

(22) PCT Filed: Feb. 20, 2015

(86) PCT No.: PCT/US2015/016830
§ 371 (c)(1),
(2) Date: Jul. 6, 2016

(87) PCT Pub. No.: WO2015/127210
PCT Pub. Date: Aug. 27, 2015

(65) Prior Publication Data
US 2016/0324113 A1    Nov. 10, 2016

Related U.S. Application Data

(60) Provisional application No. 61/942,964, filed on Feb. 21, 2014.

(51) Int. Cl.
*A01H 15/00* (2006.01)
*A01G 18/00* (2018.01)

(52) U.S. Cl.
CPC ............ *A01H 15/00* (2013.01); *A01G 18/00* (2018.02)

(58) Field of Classification Search
CPC .................................................... A01H 15/00
See application file for complete search history.

(56) References Cited

U.S. PATENT DOCUMENTS

| 7,608,760 | B2 * | 10/2009 | Robles ................... A01H 15/00 47/1.1 |
|---|---|---|---|
| 9,017,988 | B1 | 4/2015 | Kerrigan et al. |
| 9,642,333 | B2 * | 5/2017 | Kerrigan ................ A01H 15/00 |
| 2010/0212042 | A1 | 8/2010 | Robles et al. |
| 2015/0216127 | A1 | 8/2015 | Kerrigan et al. |
| 2015/0216128 | A1 | 8/2015 | Kerrigan et al. |
| 2015/0237821 | A1 | 8/2015 | Kerrigan et al. |

OTHER PUBLICATIONS

Sonnenberg et al Applied and Environmental Microbiology vol. 65, No. 8, pp. 3347-3353 (Year: 1999).*
Sonnenberg et al Proceedings of the 7th International Conference on Mushroom Biology and Mushroom Products Section: Genomics, Genetics and Breeding pp. 7-15 (Year: 2011).*
Kerrigan et al Genetics vol. 133, pp. 225-236 (Year: 1993).*
Richard W. Kerrigan, et al; Meiotic Behavior and Linkage Relationships in the Secondarily Homothallic Fungus Argaricus Bisporus; 1993 by the Genetics Society of America; 12 pages.
Emmanuelle Morin, et al; Environmental Sciences; 4146-4148, PNAS, Mar. 5. 2013, vol. 110, No. 10; 9 Pages.
Micheline Imbernon, et al.; BSN, The primary determinant of Basidial Spore number and reproductive mode in Agaricus bisporus, maps to choromosome I; Mycologia, 13 Pages.
A.J. Velco, Jr. et al.; Expression of Novel Genes in Agaricus Bisporus Using an Agrobacterium-mediated Transformation Technique; 4 pages.
D.M. Beyer, et al.; First Report of Syzgites megalocarpus (Mucorales) Web Mold on the Commercial Portabella Button Mushroom *Agaricus Bisporus* in North America; Jan. 2013; vol. 97, No. 1, p. 142; 2 pages.

* cited by examiner

*Primary Examiner* — David H Kruse
(74) *Attorney, Agent, or Firm* — Renner Kenner Greive Bobak Taylor & Weber

(57) ABSTRACT

A culture of the *Agaricus bisporus* strain B12998 is provided, the culture of the strain B12998 having been deposited under the NRRL Accession Number 50902. Other embodiments include a hybrid strain of *Agaricus bisporus* having BP-1 as one parent and an OW, SW, HW or experimental BW strain as a second parent. Still other embodiments include a hybrid strain of *Agaricus bisporus* having strain B12998 as at least one parent. Methods are provided for obtaining offspring including homokaryotic lines from select hybrid strain cultures of *Agaricus bisporus*, as well as methods and processes for producing hybrid mushroom cultures. A method of mushroom strain development is further provided.

15 Claims, No Drawings

Specification includes a Sequence Listing.

SEQUENCE LISTING

<160> NUMBER OF SEQ ID NOS: 12

<210> SEQ ID NO 1
<211> LENGTH: 18
<212> TYPE: DNA
<213> ORGANISM: Agaricus bisporus

<400> SEQUENCE: 1
aggcryccca tcttcasc                                                  18

<210> SEQ ID NO 2
<211> LENGTH: 17
<212> TYPE: DNA
<213> ORGANISM: Agaricus bisporus

<400> SEQUENCE: 2
gttcgacgac ggactgc                                                   17

<210> SEQ ID NO 3
<211> LENGTH: 19
<212> TYPE: DNA
<213> ORGANISM: Agaricus bisporus

<400> SEQUENCE: 3

-continued

```
tccgtaggtg aacctgcgg                                              19

<210> SEQ ID NO 4
<211> LENGTH: 20
<212> TYPE: DNA
<213> ORGANISM: Agaricus bisporus

<400> SEQUENCE: 4
tcctccgctt attgatatgc                                             20

<210> SEQ ID NO 5
<211> LENGTH: 23
<212> TYPE: DNA
<213> ORGANISM: Agaricus bisporus

<400> SEQUENCE: 5
aytcrcaama acataccttc aac                                         23

<210> SEQ ID NO 6
<211> LENGTH: 18
<212> TYPE: DNA
<213> ORGANISM: Agaricus bisporus

<400> SEQUENCE: 6
cattcggcga ttttctca                                               18

<210> SEQ ID NO 7
<211> LENGTH: 21
<212> TYPE: DNA
<213> ORGANISM: Agaricus bisporus

<400> SEQUENCE: 7
gacgatgcgg gactggtgga t                                           21

<210> SEQ ID NO 8
<211> LENGTH: 23
<212> TYPE: DNA
<213> ORGANISM: Agaricus bisporus

<400> SEQUENCE: 8
ggtctggcct acrggagtgt tgt                                         23

<210> SEQ ID NO 9
<211> LENGTH: 23
<212> TYPE: DNA
<213> ORGANISM: Agaricus bisporus

<400> SEQUENCE: 9
ccgccagcac aaggaatcaa atg                                         23

<210> SEQ ID NO 10
<211> LENGTH: 23
<212> TYPE: DNA
<213> ORGANISM: Agaricus bisporus

<400> SEQUENCE: 10
tcagtcggcc ctcaaaacag tcg                                         23

<210> SEQ ID NO 11
<211> LENGTH: 22
<212> TYPE: DNA
<213> ORGANISM: Agaricus bisporus
```

```
<400> SEQUENCE: 11
tcgggtggtt gcaactgaaa ag                                          22

<210> SEQ ID NO 12
<211> LENGTH: 24
<212> TYPE: DNA
<213> ORGANISM: Agaricus bisporus

<400> SEQUENCE: 12
ttcctttccg ccttaattgt ttct                                        24
```

HYBRID BW-TYPE MUSHROOM STRAINS AND LINES AND METHODS AND USES THEREFOR

TECHNICAL FIELD

This invention relates generally to the field of microorganism strain development and more particularly, to the development of heterokaryotic strains and homokaryotic lines of mushroom fungus. More specifically, the present invention relates to the development of a heterokaryotic *Agaricus bisporus* mushroom fungus culture designated strain B12998, to cultures closely related to strain B12998, and to cultures descended, or otherwise derived, from strain B12998 or from closely related cultures.

SEQUENCE LISTING

The Sequence Listing file SYL.P.PC0016 Sequence Listing_ST25.txt having a size of 2097 bytes and creation date of Feb. 20, 2015, that was electronically filed with the patent application is incorporated herein by reference in its entirety.

BACKGROUND OF THE INVENTION

The edible mushroom *Agaricus bisporus* (Lange) Imbach var. *bisporus*, a microorganism belonging to the basidiomycete fungi, is widely cultivated around the world. Accordingly, development of novel hybrid mushroom strains or lines of this mushroom fungus is seen as highly desirable to the cultivated mushroom industry, particularly if those novel strains or lines can be developed to provide various desirable traits within a single strain, culture, hybrid or line.

Thus, various entities within the mushroom industry, including Sylvan America, Inc., have set up mushroom strain development programs. The goal of a mushroom strain development program is to combine, in a single strain, culture, hybrid, or line, various desirable traits. Strains currently available to the mushroom industry allow growers to produce crops of mushrooms successfully and profitably. Several factors exist that influence the degree of success and profitability achieved. Characteristics of strains that are factors that can improve producer profitability include increased productivity (higher yield or shorter cycle time), accelerated revenue capture (earlier harvest), reduced costs (for example, greater ease and speed of harvesting), reduced shrinkage (pre-sale weight loss), reduced overweighting of product in packages (extra weight of product packaged, due to particular sizes of individual mushrooms), improved consistency of crop performance responses to variations in raw materials, growing conditions and practices, superior crop performance in particular facilities, regions, etc., reduced losses to diseases including viral, bacterial and fungal disease agents, and/or reduced losses to insect and nematode pests of the crop. There also exist improvable properties of the mushroom product that increase demand in the distribution chain, and thus sales volume and/or sales price, such as improved visual appeal (more desirable coloration, shape, size, or surface texture), improved or distinct flavor characteristics, improved keeping qualities (longer persistence of desirable visual attributes), etc. Still other improvements may enhance the suitability of the mushroom crop for mechanical harvesting, canning, and/or food processing. Thus there are many characteristics by which a novel strain might be judged as superior in a particular production facility or sales market, or in the industry regionally or globally. All of these characteristics can be assessed using techniques that are well known in the art.

Novel strains are most preferably and successfully developed from unique hybridizations between homokaryotic lines, including novel lines. Thus, the need continues to exist for new lines that can be used to produce new hybrid strains of *Agaricus bisporus* mushroom cultures and microorganisms that provide improved characteristics for producer profitability and for improved mushroom products over other previous strains of *Agaricus bisporus*.

There is also a need for commercially acceptable *A. bisporus* strains with different genotypes, relative to those of other currently available commercial brown strains and derived lineage groups, particularly those of the Old Fashioned Brown (OFB) group and the Heirloom strain, for two reasons. First, the use of strains incompatible with strains of the common commercial strains and their derived lineage groups is known to retard the spread of viral diseases between crops of different strains. The incompatibility phenotype can be assessed using techniques that are well known in the art. Second, it is well understood that when an agricultural crop industry relies extensively on a single genetic lineage (i.e., creates a commercial monoculture as now exists for the white-capped U1 lineage of *A. bisporus*, and which may exist for the brown-capped Heirloom strain), there is an increased risk of unpredictable, catastrophic crop failure on a facility-wide or even industry-wide scale. Therefore from a risk management and food security perspective, it is highly desirable to simultaneously provide both genetic diversification and commercially acceptable performance and crop characteristics. The use of novel lines that incorporate DNA from non-cultivar stocks provides important genetic diversification of the strain pool used to produce crops of cultivated *A. bisporus* mushrooms.

Circa 1980, the first two white hybrid strains of *A. bisporus*, developed by a laboratory at Horst, the Netherlands, were introduced into commercial cultivation. These two "Horst" strains, called U1 and U3, are closely related hybrid strains produced by matings between two pre-existing white cultivated strains, as per M. Imbernon et al., *Mycologia*, 88(5), 749-761 (1996), herein incorporated by reference. The two parents of U1 are the commercial strains Somycel 53 and Somycel 9.2, respectively belonging to two longstanding categorical types of strains known as the 'smooth-white' (SW) strains and the 'off-white' (OW) strains. The original homokaryons (or 'lines') obtained from the SW and OW strains, and used in the hybridization that produced the U1 strain, were designated H39 and H97 respectively; these cultures may no longer exist (A. Sonnenberg, pers. comm.).

However, a number of laboratories have deheterokaryotized the U1 strain and obtained neohaplont cultures incorporating one or the other nuclear type corresponding to those contributed by H39 or H97, as well as the mitochondrial type of U1. We refer to these two types of neohaplonts of U1 categorically as the SWNC and OWNC lines or homokaryons, respectively. An OWNC line designated 'H97' was deposited in the public culture collection of the Fungal Genetics Stock Center of Kansas, USA, by A. Sonnenberg, under the number 10389, and in the public collection of the American Type Culture Collection of Maryland, USA, under the number MYA-4626. The genome of H97 was sequenced and placed in the public domain by the Joint Genome Institute of California, USA. (See Morin et al. 2012, herein incorporated by reference). The OWNC line was also deposited by Sylvan America, Inc., on Jan. 15, 2014, with the Agricultural Research Services Culture Collection (NRRL)

1815 North University Street, Peoria, Ill. 61604 USA under the NRRL Accession No. is 50894.

One traditional type of brown-capped strain of *A. bisporus* mushroom, most often called the 'Old-Fashioned Brown' strain (or 'OFB'; examples of the OFB strain type include Sylvan's SB-65, SB-295, and RWK-2042 strains), originated as a wild strain in Europe and was the leading brown cultivar strain for many decades, even becoming the only brown cultivar in wide use in the last years of the twentieth century. A few different brown-capped hybrid strains have been developed since the 1980s, and some have enjoyed some commercial success. All publically disclosed examples of commercially relevant brown-capped hybrid strains have had both brown-capped and white-capped parents or grandparents. Hybrids having one white-capped parent line and one brown-capped parent line are categorically referred to as BW, or BW-type, hybrids. This BW-type of hybrid is heteroallelic at the PPC-1 color-determining locus on Scaffold 8 of the nuclear genome. Sylvan America, Inc. developed and patented the first BW hybrid, the X618 strain (later called SC-600 and marketed as S600), a light brown strain deposited with the Agricultural Research Services Culture Collection (NRRL) 1815 North University Street, Peoria, Ill. 61604 USA, on Feb. 18, 2014, as NRRL Accession No. 50906, and later a class of strains including the BW hybrid J10263 strain, which is sporeless (see WIPO Publication No. PCT/US2010/042289, filed Jul. 16, 2010, incorporated herein by reference). Sylvan has developed numerous breeding lines and hybrid strains from these two, and from many other, BW-type hybrid strains, beginning in the 1980s. Others have developed and patented the BW hybrid Broncoh strain, which is light to medium brown. Yet others have developed and patented the hybrid strain BR06 (ATCC Accession No. PTA-6876, later believed to have been marketed as Heirloom), a dark brown strain that used the BW hybrid 4x29 or 4-29 strain (ATCC Accession No. PTA-6877) as a parent.

Robles et al. (U.S. Pat. No. 7,608,760) teach that the brown strain BP-1, obtained by R. W. Kerrigan circa 1990, has a "difficult genetic background" and that diverse matings of BP-1 to diverse other strains almost invariably produced hybrids lacking "acceptable agronomic characteristics". They further teach that among matings of BP-1 to other strains, only in matings to a special "bridging cross strain" derived from mating one commercial white strain parent and one commercial brown strain parent, was an acceptably useful hybrid strain obtained. Thus a problem in the art has been the difficulty encountered in using genetic material of strain BP-1 in any strain development program, except in the restricted application taught by Robles et al. Thus, the need exists for distinct, useful and valuable methods whereby, and for products wherein, the genetic material of BP-1 may be combined with other genetic material of *A. bisporus* in matings that do not require the mating of BP-1 to a special "bridging cross strain" as taught in U.S. Pat. No. 7,608,760.

Cultures are the means by which the mushroom strain developers prepare, maintain, and propagate their microorganisms. Cultures of *Agaricus*, like those of other microorganisms, are prepared, maintained, propagated and stored on sterile media using various microbiological laboratory methods and techniques. Sterile tools and aseptic techniques are used within clean rooms or sterile transfer hoods to manipulate cells of pure cultures for various purposes including clonal propagation and for the development of new strains using diverse techniques. Commercial culture inocula including mushroom 'spawn' and 'casing inoculum' are also prepared using large-scale microbiological production methods, and are provided to the end user as pure cultures contained within sterile packaging.

One use of such cultures is to produce mushrooms. Mushrooms are cultivated commercially within purpose-built structures on dedicated farms. While there are many variations on methods, the following description is typical. Compost prepared from lignocellulosic material such as straw, augmented with nitrogenous material, is finished and pasteurized within a suitable facility. Mushroom spawn, which comprises a sterilized friable 'carrier substrate' onto which a pure culture of one mushroom strain has been aseptically incorporated via inoculum and then propagated, is mixed with the pasteurized compost and is incubated for approximately 13 to about 19 days at a controlled temperature, during which time the mycelium of the mushroom culture colonizes the entire mass of compost and begins to digest it. A non-nutritive 'casing layer' of material such as peat is then placed over the compost to a depth of from about 1.5 to about 2 inches. Additional 'casing inoculum' incorporating the same mushroom culture may be incorporated into the casing layer to accelerate the formation and harvesting of mushrooms, and improve uniformity of the distribution of mycelium and mushrooms in and on the casing surface. Environmental conditions, including temperature and humidity, in the cropping facility are then carefully managed to promote and control the transition of the culture from vegetative to reproductive growth at the casing/air interface. In a further about 13 to about 18 days after casing, mushrooms will have developed to the correct stage for harvest and sale. A flush of mushrooms comprising the original culture will be picked over a 3 to 4 day period. Additional flushes of mushrooms appear at about weekly intervals. Commercially, two or three flushes of mushrooms are produced and harvested before the compost is removed and replaced in the cropping facility.

*Agaricus bisporus* has a reproductive syndrome known as amphithallism, in which two distinct life cycles operate concurrently. As in other fungi, the reproductive propagule is a spore. *Agaricus* produces spores meiotically, on a meiosporangium known as a basidium. In a first life cycle, *A. bisporus* spores each receive a single haploid postmeiotic nucleus; these spores are competent to mate but not competent to produce mushrooms. These haploid spores germinate to produce homokaryotic offspring or lines which can mate with other compatible homokaryons to produce novel hybrid heterokaryons that are competent to produce mushrooms. Heterokaryons generally exhibit much less ability to mate than do homokaryons. This lifecycle is called heteromixis, or more commonly, outbreeding. This life cycle operates but typically does not predominate in strains of *Agaricus bisporus* var. *bisporus*.

A second, inbreeding life cycle called intramixis predominates in most strains of *Agaricus bisporus* var. *bisporus*. Most spores receive two post-meiotic nuclei, and most such pairs of nuclei consist of Non-Sister Nuclear Pairs (NSNPs) which have a heteroallelic genotype at most or all centromeric-linked loci including the MAT locus. That MAT genotype determines the heterokaryotic phenotype of these offspring, which are reproductively competent and can produce a crop of mushrooms. Unusually among eukaryotes, relatively little chromosomal crossing-over is observed to have occurred in postmeiotic offspring of *Agaricus bisporus*; empirically, very little heteroallelism (analogous to heterozygosity) is lost among heterokaryotic offspring of a heterokaryotic strain. Consequently, parental and offspring heterokaryotic genotypes and phenotypes tend to closely resemble each other, as noted above. For this reason, essential derivation, e.g., the production of Essentially Derived Varieties (EDVs), is a familiar strain development technique among commercial mushroom spawn producers.

Another use of cultures of mushroom strains is to produce spores from mushrooms. Spores in turn can be used to produce offspring which are or may be useful in programs to develop new and improved strains of mushroom. Spores from mushrooms may be aseptically collected on sterile material, suspended in sterile water at various dilutions, and plated onto sterile agar growth media in order to produce germinated spores and the cultures incorporated within the spores. A preferred technique is to have within the enclosed petri plate a living *Agaricus* culture which may stimulate spore germination via the diffusion of a volatile pheromone. Germinated spores may be isolated under a microscope using sterile microtools such as steel needles, onto fresh nutrient agar plates. Using this method, heterokaryotic and homokaryotic offspring of strains including strain B12998 comprising the spores and the cultures incorporated within the spores of strains including strain B12998 may be obtained. Homokaryotic lines may in turn be used in matings to other lines to produce novel hybrid strains of mushrooms.

Therefore, the need exists for the development of new *Agaricus bisporus* lines that meet the needs and desires of mushroom producers, marketers and consumers. More particularly, the need exists for successful methods for the use of strain BP-1 that do not require the use of a special "bridging cross strain" in a mating to BP-1.

SUMMARY OF THE INVENTION

The present invention is directed generally to new types of hybrid *Agaricus bisporus* strains, and more particularly to a new and distinct heterokaryotic strain of *Agaricus bisporus* designated B12998, and processes for using the strain designated B12998 and other related strains. A deposit of a culture of the *Agaricus bisporus* strain B12998, as disclosed herein, has been made with the Agricultural Research Services Culture Collection (NRRL) 1815 North University Street, Peoria, Ill. 61604 USA. The date of deposit was Feb. 18, 2014. The culture deposited was taken from the same culture maintained by Sylvan America, Inc., Kittanning, Pa., USA, the assignee of record, since prior to the filing date of this application. All restrictions upon the deposit have been removed, and the deposit is intended to meet all deposit requirements of the U.S. Patent and Trademark Office, including 37 C.F.R. Sec. 1.801-1.809, and all deposit requirements under the Budapest Treaty. The NRRL Accession No. is 50902. The deposit will be maintained in the depository for a period of 30 years, or 5 years after the last request, or for the effective life of the patent, whichever is longer, and will be replaced as necessary during that period. The culture will be irrevocably and without restriction or condition released to the public upon the filing of the patent application or upon the issuance of a patent, whichever is required by the applicable patent laws.

Uses of the culture of mushroom strain B12998 (and equally of cultures of strains related to B12998 as described in the present application) include, among many other things, the production of homokaryotic lines and other offspring from spores of B12998, the production of hybrid mushroom cultures incorporating lines obtained from strain B12998, the production of mushrooms from cultures incorporating lines obtained from B12998, and the production of mushroom parts from cultures incorporating lines obtained from strain B12998. Still other uses include processes for making a mushroom culture that comprise mating homokaryotic *Agaricus bisporus* lines obtained from strain B12998 with another mushroom culture and processes for making a mushroom culture containing in its genetic material one or more traits introgressed into lines obtained from B12998 through introgressive trait conversion or transformation, and to the mushroom cultures, mushrooms, and mushroom parts produced by such introgression. Further, the invention may include a hybrid mushroom culture, mushroom, mushroom part, including a spore, or culture part produced by mating a homokaryotic line obtained from strain B12998, or an introgressed trait conversion of a line obtained from strain B12998, with another mushroom culture. Still other uses of the present invention include the production of homokaryotic mushroom lines derived from mushroom lines obtained from strain B12998, as well as the processes for making other homokaryotic mushroom lines derived from mushroom lines obtained from strain B12998, and to the production of the inbred mushroom lines and their parts derived by the use of those processes.

All of the foregoing uses are available equally for lines obtained from hybrid strains having as one parent the same BP-1 (or BP-1 derived lineage group) strain as a first parent, and as the second parent the same white strain parent Somycel 76 of strain B12998, or a usefully equivalent (i.e., either identical with, belonging to the same derived lineage group as, or functionally similar to) white strain. These include hybrid strains obtained from matings of lines obtained from strain BP-1 with lines obtained from any traditional Off-white (=OW) strain such as, for example, Somycel 9.2, Somycel 76 or Somycel 611. These and other OW strains form a derived lineage group (of EDVs) which share a common genetic identity, and are functionally equivalent and interchangeable for the purposes of the invention. In addition to strain B12998, Sylvan has made 173 other matings of lines obtained from Off-white (OW) strains Somycel 76, Somycel 611, or Somycel 9.2 to lines of BP-1, to obtain a total of 173 hybrid strains of the BW type which are each genetically distinct and which are 'sisters' to B12998. Sylvan has further obtained homokaryotic lines from among these hybrids. Strain Somycel 76 fairly represents all OW strains. A deposit of a culture of hybrid strain Somycel 76, as disclosed herein, has been made with the Agricultural Research Services Culture Collection (NRRL) 1815 North University Street, Peoria, Ill. 61604 USA. The date of deposit was Feb. 18, 2014. The culture deposited was taken from the same culture maintained by Sylvan America, Inc., Kittanning, Pa., since prior to the filing date of this application. All restrictions upon the deposit have been removed, and the deposit is intended to meet all deposit requirements of the U.S. Patent and Trademark Office, including 37 C.F.R. Sec. 1.801-1.809, and all deposit requirements under the Budapest Treaty. The NRRL Accession No. is 50903. The deposit will be maintained in the depository for a period of 30 years, or 5 years after the last request, or for the effective life of the patent, whichever is longer, and will be replaced as necessary during that period. The strain will be irrevocably and without restriction or condition released to the public upon the filing of the priority application or upon the issuance of a patent on this strain according to the patent laws.

Likewise, a deposit of a culture of the *Agaricus bisporus* homokaryotic line Somycel 76-s39, as disclosed herein, has been made with the Agricultural Research Services Culture Collection (NRRL) 1815 North University Street, Peoria, Ill. 61604 USA. The date of deposit was Feb. 18, 2014. The culture deposited was taken from the same culture maintained by Sylvan America, Inc., Kittanning, Pa., the assignee of record, since prior to the filing date of this application. All restrictions upon the deposit have been removed, and the deposit is intended to meet all deposit requirements of the U.S. Patent and Trademark Office, including 37 C.F.R. Sec. 1.801-1.809, and all deposit requirements under the Budapest Treaty. The NRRL Accession No. is 50905. The deposit will be maintained in the depository for a period of 30 years, or 5 years after the last request, or for the effective life of the patent, whichever is longer, and will be replaced as necessary during that period. The culture will be irrevocably and without restriction or condition released to the public upon filing of a priority application or upon the issuance of a patent according to the patent laws.

Table I lists, as examples, 173 hybrids strains thus far obtained by Sylvan America, Inc., having one OW parent and one BP-1 parent.

TABLE I

| Hybrid ID | Parent 1 Strain | Parent 1 Line | Parent 2 Strain | Parent 2 Line |
|---|---|---|---|---|
| B11843 | So9.2 | H97 | BP-1 | s66 |
| B11844 | So9.2 | H97 | BP-1 | s14 |
| B11845 | So9.2 | H97 | BP-1 | s105 |
| B11846 | So9.2 | H97 | BP-1 | s76 |
| B11847 | So9.2 | H97 | BP-1 | s30 |
| B11848 | So9.2 | H97 | BP-1 | s35 |
| B11849 | So9.2 | H97 | BP-1 | s28 |
| B11850 | So9.2 | H97 | BP-1 | s2 |
| B12141 | So9.2 | H97 | BP-1 | s3 |
| B12148 | So9.2 | H97 | BP-1 | s4 |
| B12155 | So9.2 | H97 | BP-1 | s11 |
| B12162 | So9.2 | H97 | BP-1 | s13 |
| B12169 | So9.2 | H97 | BP-1 | s20 |
| B12176 | So9.2 | H97 | BP-1 | s47 |
| B12183 | So9.2 | H97 | BP-1 | s49 |
| B12190 | So9.2 | H97 | BP-1 | s51 |
| B12197 | So9.2 | H97 | BP-1 | s53 |
| B12204 | So9.2 | H97 | BP-1 | s64 |
| B12211 | So9.2 | H97 | BP-1 | s71 |
| B12218 | So9.2 | H97 | BP-1 | s75 |
| B12225 | So9.2 | H97 | BP-1 | s90 |
| B12232 | So9.2 | H97 | BP-1 | s99 |
| B12239 | So9.2 | H97 | BP-1 | s102 |
| B12246 | So9.2 | H97 | BP-1 | s107 |
| B12253 | So9.2 | H97 | BP-1 | s111 |
| B12260 | So9.2 | H97 | BP-1 | s113 |
| B12267 | So9.2 | H97 | BP-1 | s120 |
| B12274 | So9.2 | H97 | BP-1 | s121 |
| B12431 | So76 | s4 | BP-1 | s66 |
| B12432 | So76 | s14 | BP-1 | s66 |
| B12433 | So76 | s18 | BP-1 | s66 |
| B12434 | So76 | s36 | BP-1 | s66 |
| B12435 | So76 | s59 | BP-1 | s66 |
| B12436 | So76 | s65 | BP-1 | s66 |
| B12437 | So76 | s68 | BP-1 | s66 |
| B12438 | So76 | s75 | BP-1 | s66 |
| B12439 | So76 | s77 | BP-1 | s66 |
| B12440 | So76 | s78 | BP-1 | s66 |
| B12441 | So76 | s85 | BP-1 | s66 |
| B12442 | So76 | s86 | BP-1 | s66 |
| B12443 | So76 | s88 | BP-1 | s66 |
| B12444 | So76 | s94 | BP-1 | s66 |
| B12445 | So76 | s4 | BP-1 | s30 |
| B12446 | So76 | s14 | BP-1 | s30 |
| B12447 | So76 | s18 | BP-1 | s30 |
| B12448 | So76 | s36 | BP-1 | s30 |
| B12449 | So76 | s59 | BP-1 | s30 |
| B12450 | So76 | s65 | BP-1 | s30 |
| B12451 | So76 | s68 | BP-1 | s30 |
| B12452 | So76 | s75 | BP-1 | s30 |
| B12453 | So76 | s77 | BP-1 | s30 |
| B12454 | So76 | s78 | BP-1 | s30 |
| B12455 | So76 | s85 | BP-1 | s30 |
| B12456 | So76 | s86 | BP-1 | s30 |
| B12457 | So76 | s88 | BP-1 | s30 |

TABLE I-continued

| Hybrid ID | Parent 1 Strain | Parent 1 Line | Parent 2 Strain | Parent 2 Line |
|---|---|---|---|---|
| B12458 | So76 | s94 | BP-1 | s30 |
| B12465 | So611 | s3 | BP-1 | s66 |
| B12466 | So611 | s4 | BP-1 | s66 |
| B12467 | So611 | s14 | BP-1 | s66 |
| B12469 | So611 | s22 | BP-1 | s66 |
| B12470 | So611 | s25 | BP-1 | s66 |
| B12471 | So611 | s3 | BP-1 | s30 |
| B12472 | So611 | s4 | BP-1 | s30 |
| B12473 | So611 | s14 | BP-1 | s30 |
| B12475 | So611 | s22 | BP-1 | s30 |
| B12476 | So611 | s25 | BP-1 | s30 |
| B12485 | So9.2 | H97 | BP-1 | s10 |
| B12486 | So9.2 | H97 | BP-1 | s52 |
| B12487 | So9.2 | H97 | BP-1 | s63 |
| B12488 | So9.2 | H97 | BP-1 | s93 |
| B12837 | So76 | s8b | BP-1 | s66 |
| B12838 | So76 | s12a | BP-1 | s66 |
| B12839 | So76 | s12b | BP-1 | s66 |
| B12840 | So76 | s16 | BP-1 | s66 |
| B12841 | So76 | s20 | BP-1 | s66 |
| B12842 | So76 | s24 | BP-1 | s66 |
| B12843 | So76 | s30 | BP-1 | s66 |
| B12844 | So76 | s33a | BP-1 | s66 |
| B12845 | So76 | s43a | BP-1 | s66 |
| B12846 | So76 | s43b | BP-1 | s66 |
| B12847 | So76 | s47 | BP-1 | s66 |
| B12848 | So76 | s67a | BP-1 | s66 |
| B12849 | So76 | s80a | BP-1 | s66 |
| B12850 | So76 | s80b | BP-1 | s66 |
| B12851 | So76 | s91 | BP-1 | s66 |
| B12852 | So76 | s92 | BP-1 | s66 |
| B12853 | So76 | s93 | BP-1 | s66 |
| B12854 | So76 | s95 | BP-1 | s66 |
| B12855 | So76 | s6 | BP-1 | s66 |
| B12858 | So76 | s11 | BP-1 | s66 |
| B12859 | So76 | s13 | BP-1 | s99 |
| B12860 | So76 | s22 | BP-1 | s99 |
| B12862 | So76 | s32 | BP-1 | s99 |
| B12863 | So76 | s34 | BP-1 | s99 |
| B12864 | So76 | s39 | BP-1 | s99 |
| B12865 | So76 | s61 | BP-1 | s99 |
| B12866 | So76 | s72 | BP-1 | s99 |
| B12867 | So76 | s81 | BP-1 | s99 |
| B12868 | So76 | s84 | BP-1 | s99 |
| B12869 | So76 | s87 | BP-1 | s99 |
| B12870 | So76 | s90 | BP-1 | s99 |
| B12871 | So76 | s96 | BP-1 | s99 |
| B12872 | So76 | s8a | BP-1 | s99 |
| B12873 | So76 | s21a | BP-1 | s99 |
| B12874 | So76 | s26a | BP-1 | s99 |
| B12875 | So76 | s29a | BP-1 | s99 |
| B12876 | So76 | s29b | BP-1 | s99 |
| B12877 | So76 | s40a | BP-1 | s99 |
| B12878 | So76 | s67c | BP-1 | s99 |
| B12879 | So76 | s82a | BP-1 | s99 |
| B12880 | So76 | s82b | BP-1 | s99 |
| B12969 | So611 | s2a | BP-1 | s66 |
| B12970 | So611 | s7b | BP-1 | s66 |
| B12971 | So611 | s15a | BP-1 | s66 |
| B12972 | So611 | s15b | BP-1 | s66 |
| B12981 | So76 | s14 | BP-1 | s2 |
| B12982 | So76 | s14 | BP-1 | s28 |
| B12983 | So76 | s14 | BP-1 | s66 |
| B12984 | So76 | s14 | BP-1 | s13 |
| B12985 | So76 | s14 | BP-1 | s47 |
| B12986 | So76 | s14 | BP-1 | s53 |
| B12987 | So76 | s14 | BP-1 | s51 |
| B12988 | So76 | s14 | BP-1 | s71 |
| B12989 | So76 | s14 | BP-1 | s99 |
| B12990 | So76 | s14 | BP-1 | s107 |
| B12991 | So76 | s14 | BP-1 | s111 |
| B12992 | So76 | s39 | BP-1 | s2 |
| B12993 | So76 | s39 | BP-1 | s28 |
| B12994 | So76 | s39 | BP-1 | s66 |
| B12995 | So76 | s39 | BP-1 | s13 |
| B12996 | So76 | s39 | BP-1 | s47 |

TABLE I-continued

| Hybrid | Parent 1 | | Parent 2 | |
|---|---|---|---|---|
| ID | Strain | Line | Strain | Line |
| B12997 | So76 | s39 | BP-1 | s53 |
| B12998 | So76 | s39 | BP-1 | s51 |
| B12999 | So76 | s39 | BP-1 | s71 |
| B13000 | So76 | s39 | BP-1 | s99 |
| B13001 | So76 | s39 | BP-1 | s107 |
| B13002 | So76 | s39 | BP-1 | s111 |
| B13003 | So611 | s4 | BP-1 | s2 |
| B13004 | So611 | s4 | BP-1 | s28 |
| B13005 | So611 | s4 | BP-1 | s66 |
| B13006 | So611 | s4 | BP-1 | s13 |
| B13007 | So611 | s4 | BP-1 | s47 |
| B13008 | So611 | s4 | BP-1 | s53 |
| B13009 | So611 | s4 | BP-1 | s51 |
| B13010 | So611 | s4 | BP-1 | s71 |
| B13011 | So611 | s4 | BP-1 | s99 |
| B13012 | So611 | s4 | BP-1 | s107 |
| B13013 | So611 | s4 | BP-1 | s111 |
| B13025 | So611 | s22 | BP-1 | s2 |
| B13026 | So611 | s22 | BP-1 | s28 |
| B13027 | So611 | s22 | BP-1 | s66 |
| B13028 | So611 | s22 | BP-1 | s13 |
| B13029 | So611 | s22 | BP-1 | s47 |
| B13030 | So611 | s22 | BP-1 | s53 |
| B13031 | So611 | s22 | BP-1 | s51 |
| B13032 | So611 | s22 | BP-1 | s71 |
| B13033 | So611 | s22 | BP-1 | s99 |
| B13034 | So611 | s22 | BP-1 | s107 |
| B13035 | So611 | s22 | BP-1 | s111 |
| B13036 | So611 | s7b | BP-1 | s2 |
| B13037 | So611 | s7b | BP-1 | s28 |
| B13038 | So611 | s7b | BP-1 | s66 |
| B13039 | So611 | s7b | BP-1 | s13 |
| B13040 | So611 | s7b | BP-1 | s47 |
| B13041 | So611 | s7b | BP-1 | s53 |
| B13042 | So611 | s7b | BP-1 | s51 |
| B13043 | So611 | s7b | BP-1 | s71 |
| B13044 | So611 | s7b | BP-1 | s99 |
| B13045 | So611 | s7b | BP-1 | s107 |
| B13046 | So611 | s7b | BP-1 | s111 |
| B13167 | So611 | s2a | BP-1 | s99 |
| B13168 | So611 | s7b | BP-1 | s99 |
| B13169 | So611 | s15a | BP-1 | s99 |
| B13170 | So611 | s15b | BP-1 | s99 |

All of the foregoing uses are available equally for lines obtained from hybrid strains having as one parent strain the same BP-1 (or BP-1 derived lineage group) parent strain as hybrid strain B12998, and also a second parent strain which is a Smooth-white (=SW) strain. These include hybrid strains obtained from matings of lines obtained from strain BP-1 with lines obtained from the traditional Smooth-white strain and/or from the derived lineage group (of EDVs) including strain Somycel 53, which strains share a common genetic identity, and are functionally equivalent and interchangeable for the purposes of the invention.

Sylvan has made 138 matings between lines of Somycel 53, a Smooth-white strain, to lines of BP-1, to obtain a total of 138 additional novel BW-type hybrid strains from which homokaryotic lines may be obtained. Strain Somycel 53 fairly represents all SW strains belonging to the SW derived lineage group. A deposit of a culture of hybrid strain Somycel 53, as disclosed herein, has been made with the Agricultural Research Services Culture Collection (NRRL) 1815 North University Street, Peoria, Ill. 61604 USA. The date of deposit was Feb. 18, 2014. The culture deposited was taken from the same culture maintained by Sylvan America, Inc., Kittanning, Pa., since prior to the filing date of this application. All restrictions upon the deposit have been removed, and the deposit is intended to meet all deposit requirements of the U.S. Patent and Trademark Office, including 37 C.F.R. Sec. 1.801-1.809, and all deposit requirements under the Budapest Treaty. The NRRL Accession No. is 50904. The deposit will be maintained in the depository for a period of 30 years, or 5 years after the last request, or for the effective life of the patent, whichever is longer, and will be replaced as necessary during that period. The strain will be irrevocably and without restriction or condition released to the public upon the filing of the priority application or upon the issuance of a patent on this strain according to the patent laws.

Table II lists, as examples, 138 hybrids strains thus far obtained by Sylvan America, Inc., having one SW parent and one BP-1 parent.

TABLE II

| Hybrid | Parent 1 | | Parent 2 | |
|---|---|---|---|---|
| ID | Strain | Line | Strain | Line |
| B11867 | So53 | H39 | BP-1 | s66 |
| B11868 | So53 | H39 | BP-1 | s14 |
| B11869 | So53 | H39 | BP-1 | s105 |
| B11870 | So53 | H39 | BP-1 | s76 |
| B11871 | So53 | H39 | BP-1 | s30 |
| B11872 | So53 | H39 | BP-1 | s35 |
| B11873 | So53 | H39 | BP-1 | s28 |
| B11874 | So53 | H39 | BP-1 | s2 |
| B12142 | So53 | H39 | BP-1 | s3 |
| B12149 | So53 | H39 | BP-1 | s4 |
| B12156 | So53 | H39 | BP-1 | s11 |
| B12163 | So53 | H39 | BP-1 | s13 |
| B12170 | So53 | H39 | BP-1 | s20 |
| B12177 | So53 | H39 | BP-1 | s47 |
| B12184 | So53 | H39 | BP-1 | s49 |
| B12191 | So53 | H39 | BP-1 | s51 |
| B12198 | So53 | H39 | BP-1 | s53 |
| B12205 | So53 | H39 | BP-1 | s64 |
| B12212 | So53 | H39 | BP-1 | s71 |
| B12219 | So53 | H39 | BP-1 | s75 |
| B12226 | So53 | H39 | BP-1 | s90 |
| B12233 | So53 | H39 | BP-1 | s99 |
| B12240 | So53 | H39 | BP-1 | s102 |
| B12247 | So53 | H39 | BP-1 | s107 |
| B12254 | So53 | H39 | BP-1 | s111 |
| B12261 | So53 | H39 | BP-1 | s113 |
| B12268 | So53 | H39 | BP-1 | s120 |
| B12275 | So53 | H39 | BP-1 | s121 |
| B12391 | So53 | s85 | BP-1 | s66 |
| B12392 | So53 | s87 | BP-1 | s66 |
| B12393 | So53 | s94 | BP-1 | s66 |
| B12394 | So53 | s105 | BP-1 | s66 |
| B12395 | So53 | s106 | BP-1 | s66 |
| B12396 | So53 | s113 | BP-1 | s66 |
| B12397 | So53 | s116 | BP-1 | s66 |
| B12398 | So53 | s117 | BP-1 | s66 |
| B12399 | So53 | s121 | BP-1 | s66 |
| B12400 | So53 | s129 | BP-1 | s66 |
| B12401 | So53 | s141 | BP-1 | s66 |
| B12402 | So53 | s145 | BP-1 | s66 |
| B12403 | So53 | s148 | BP-1 | s66 |
| B12489 | So53 | H39 | BP-1 | s10 |
| B12490 | So53 | H39 | BP-1 | s52 |
| B12491 | So53 | H39 | BP-1 | s63 |
| B12492 | So53 | H39 | BP-1 | s93 |
| B12739 | So53 | s22 | BP-1 | s66 |
| B12740 | So53 | s56 | BP-1 | s66 |
| B12741 | So53 | s69 | BP-1 | s66 |
| B12742 | So53 | s70 | BP-1 | s66 |
| B12743 | So53 | s71 | BP-1 | s66 |
| B12744 | So53 | s82a | BP-1 | s66 |
| B12745 | So53 | s88 | BP-1 | s66 |
| B12746 | So53 | s92 | BP-1 | s66 |
| B12747 | So53 | s114 | BP-1 | s66 |
| B12748 | So53 | s6 | BP-1 | s66 |
| B12749 | So53 | s26 | BP-1 | s66 |
| B12750 | So53 | s27 | BP-1 | s66 |
| B12751 | So53 | s32 | BP-1 | s66 |

TABLE II-continued

| Hybrid ID | Parent 1 Strain | Parent 1 Line | Parent 2 Strain | Parent 2 Line |
|---|---|---|---|---|
| B12752 | So53 | s33 | BP-1 | s66 |
| B12753 | So53 | s35 | BP-1 | s66 |
| B12754 | So53 | s36 | BP-1 | s66 |
| B12755 | So53 | s37 | BP-1 | s66 |
| B12756 | So53 | s38 | BP-1 | s66 |
| B12757 | So53 | s39 | BP-1 | s66 |
| B12758 | So53 | s43 | BP-1 | s66 |
| B12759 | So53 | s46 | BP-1 | s66 |
| B12760 | So53 | s60 | BP-1 | s66 |
| B12761 | So53 | s61 | BP-1 | s66 |
| B12762 | So53 | s65 | BP-1 | s66 |
| B12763 | So53 | s66 | BP-1 | s66 |
| B12764 | So53 | s73 | BP-1 | s66 |
| B12765 | So53 | s74 | BP-1 | s66 |
| B12766 | So53 | s75 | BP-1 | s66 |
| B12767 | So53 | s86 | BP-1 | s66 |
| B12768 | So53 | s96b | BP-1 | s66 |
| B12769 | So53 | s98a | BP-1 | s66 |
| B12770 | So53 | s107 | BP-1 | s66 |
| B12771 | So53 | s109 | BP-1 | s66 |
| B12772 | So53 | s111a | BP-1 | s66 |
| B12773 | So53 | s113a | BP-1 | s66 |
| B12774 | So53 | s126 | BP-1 | s66 |
| B12775 | So53 | s127 | BP-1 | s66 |
| B12776 | So53 | s132 | BP-1 | s66 |
| B12777 | So53 | s143a | BP-1 | s66 |
| B12778 | So53 | s143b | BP-1 | s66 |
| B12779 | So53 | s149 | BP-1 | s66 |
| B12780 | So53 | s7 | BP-1 | s66 |
| B12781 | So53 | s14 | BP-1 | s66 |
| B12782 | So53 | s51 | BP-1 | s66 |
| B12783 | So53 | s96a | BP-1 | s66 |
| B12784 | So53 | s98b | BP-1 | s66 |
| B12785 | So53 | s131 | BP-1 | s66 |
| B12786 | So53 | s135a | BP-1 | s66 |
| B12787 | So53 | s135b | BP-1 | s66 |
| B13596 | So53 | s105 | BP-1 | s13 |
| B13597 | So53 | s105 | BP-1 | s53 |
| B13598 | So53 | s105 | BP-1 | s99 |
| B13599 | So53 | s105 | BP-1 | s2 |
| B13600 | So53 | s105 | BP-1 | s14 |
| B13601 | So53 | s105 | BP-1 | s75 |
| B13602 | So53 | s105 | BP-1 | s102 |
| B13603 | So53 | s143A | BP-1 | s13 |
| B13604 | So53 | s143A | BP-1 | s53 |
| B13605 | So53 | s143A | BP-1 | s99 |
| B13606 | So53 | s143A | BP-1 | s2 |
| B13607 | So53 | s143A | BP-1 | s14 |
| B13608 | So53 | s143A | BP-1 | s75 |
| B13609 | So53 | s143A | BP-1 | s102 |
| B13610 | So53 | s26 | BP-1 | s13 |
| B13611 | So53 | s26 | BP-1 | s53 |
| B13612 | So53 | s26 | BP-1 | s99 |
| B13613 | So53 | s26 | BP-1 | s2 |
| B13614 | So53 | s26 | BP-1 | s14 |
| B13615 | So53 | s26 | BP-1 | s75 |
| B13616 | So53 | s26 | BP-1 | s102 |
| B13617 | So53 | s27 | BP-1 | s13 |
| B13618 | So53 | s27 | BP-1 | s53 |
| B13619 | So53 | s27 | BP-1 | s99 |
| B13620 | So53 | s27 | BP-1 | s2 |
| B13621 | So53 | s27 | BP-1 | s14 |
| B13622 | So53 | s27 | BP-1 | s75 |
| B13623 | So53 | s27 | BP-1 | s102 |
| B13624 | So53 | s87 | BP-1 | s13 |
| B13625 | So53 | s87 | BP-1 | s53 |
| B13626 | So53 | s87 | BP-1 | s99 |
| B13627 | So53 | s87 | BP-1 | s2 |
| B13628 | So53 | s94 | BP-1 | s13 |
| B13629 | So53 | s94 | BP-1 | s53 |
| B13630 | So53 | s94 | BP-1 | s99 |
| B13631 | So53 | s94 | BP-1 | s2 |
| B13632 | So53 | s6 | BP-1 | s13 |
| B13633 | So53 | s6 | BP-1 | s53 |
| B13634 | So53 | s6 | BP-1 | s99 |
| B13635 | So53 | s6 | BP-1 | s2 |
| B13636 | So53 | s56 | BP-1 | s13 |
| B13637 | So53 | s56 | BP-1 | s53 |
| B13638 | So53 | s56 | BP-1 | s99 |
| B13639 | So53 | s56 | BP-1 | s2 |

All of the foregoing uses are available equally for lines obtained from hybrid strains having as one parent strain the same BP-1 (or BP-1 derived lineage group) parent strain as hybrid strain B12998, and also a second parent strain which is a Hybrid White (=HW) stain. These include hybrid strains obtained from matings of lines obtained from strain BP-1 with lines obtained from experimental and/or commercial Hybrid White strains and/or from the derived lineage group (of EDVs) of Hybrid White strains, which strains, within any derived lineage group, share a common genetic identity, and are functionally equivalent and interchangeable for the purposes of the invention. Examples of known commercial and experimental HW strains, which number into the thousands, and which may be used as parents in matings to BP-1 or to lines obtained from BP-1 include U1, U3, A-15, S-130, AS-2796, AS-3003, B7970, J9277, J10102, J10165, J11500, and many other HW strains and also EDVs of those strains.

Table III lists, as examples, seven of the hybrid strains thus far obtained by Sylvan, having one HW parent, Sylvan's experimental hybrid J10165 in these examples, and one BP-1 parent:

TABLE III

| Hybrid ID | Parent 1 Strain | Parent 1 Line | Parent 2 Strain | Parent 2 Line |
|---|---|---|---|---|
| J11859 | J10165TC | s83 | BP-1 | s66 |
| J11860 | J10165TC | s83 | BP-1 | s14 |
| J11861 | J10165TC | s83 | BP-1 | s105 |
| J11862 | J10165TC | s83 | BP-1 | s76 |
| J11863 | J10165TC | s83 | BP-1 | s30 |
| J11864 | J10165TC | s83 | BP-1 | s35 |
| J11865 | J10165TC | s83 | BP-1 | s28 |

Similarly, all of the foregoing uses are available equally for lines obtained from hybrid strains having a homokaryotic line obtained from hybrid strain B12998 as at least one parent. Such hybrids more particularly include hybrid strains obtained from matings of lines obtained from strain B12998 (or from EDVs of strain B12998) with lines obtained from BW-type hybrids comprised of: sporeless strains including J10259 and J10263, Sylvan's patented BW hybrid SC-600, and select other BW-type hybrids. Sylvan has obtained at least 33 homokaryotic lines from strain B12998. These at least 33 lines have been used in at least 367 matings to diverse other lines, including to lines obtained from SW, OFB, experimental brown, and BW strains including sporeless strains including J10259 and J10263, and/or from Sylvan's patented BW hybrid SC-600, and/or other types of strains, to obtain 367 novel hybrid strain progeny of strain B12998. A deposit of a culture of the hybrid strain SC-600, as disclosed herein, has been made with the Agricultural Research Services Culture Collection (NRRL) 1815 North University Street, Peoria, Ill. 61604 USA. The date of deposit was Feb. 18, 2014. The culture deposited was taken from the same culture maintained by Sylvan America, Inc., Kittanning, Pa., since prior to the filing date of this application. All restrictions upon the deposit have been removed, and the deposit is intended to meet all deposit requirements of the U.S. Patent and Trademark Office, including 37 C.F.R. Sec. 1.801-1.809, and all deposit requirements under the Budapest Treaty. The NRRL Accession No. is 50906. The deposit will be maintained in the depository for a period of 30 years, or 5 years after the last request, or for the effective life of the patent, whichever is longer, and will be replaced as necessary during that period. The strain will be irrevocably and without restriction or condition released to the public upon the filing of the priority application or upon the issuance of a patent on this strain according to the patent laws.

Table IV provides a list of examples of homokaryotic lines thus far obtained by Sylvan America, Inc. from strain B12998 and used in matings to other lines to produce hybrid strains:

TABLE IV

B12998-s1
B12998-s3
B12998-s4
B12998-s5
B12998-s8
B12998-s9
B12998-s10
B12998-s13
B12998-s14
B12998-s15
B12998-s16
B12998-s17
B12998-s18
B12998-s24
B12998-s25
B12998-s26
B12998-s27
B12998-s29
B12998-s30
B12998-s33
B12998-s34
B12998-s39
B12998-s40
B12998-s41
B12998-s44
B12998-s47
B12998-s48
B12998-s57
B12998-s63
B12998-s67
B12998-s74
B12998-s75
B12998-s80

The genotypes at the p1n150/MAT and MFPC-1-ELF/PPC-1 loci are known for these lines.

Of the at least 367 hybrids thus far obtained by Sylvan, having B12998 as one parent, the following examples are indicative. The first mating to an OFB strain produced a hybrid strain designated B14464. The first mating to a BW strain produced a hybrid strain designated B14465. The first mating to an SW strain produced a hybrid strain designated B14466. The first mating to SC-600 produced a hybrid strain designated B15470. The first mating to a sporeless strain produced a hybrid strain designated J15467. The first mating to an experimental brown hybrid strain produced a hybrid strain designated B15483. Matings to strains in other categories produced additional hybrid strains beginning with the strain designated B15504.

With respect to spores, living spores are heterokaryons or homokaryons in a dormant state. Spores are one part of the mushroom organism. Other parts include caps, stems, gills, cells (defined as hyphal compartments incorporating nuclei, mitochondria, cytoplasm, a cell membrane, and a cell wall including crosswalls), hyphae, and mycelium. Spores may be aseptically collected on sterile material, suspended in sterile water at various dilutions, and plated onto sterile agar growth media in order to produce germinated spores and the cultures incorporated within the spores. A preferred technique is to have within the enclosed petri plate a living *Agaricus* culture which may stimulate spore germination via the diffusion of a volatile pheromone. Germinated spores may be isolated under a microscope using sterile microtools such as steel needles, onto fresh nutrient agar plates. Using this method, heterokaryotic and homokaryotic offspring of a heterokaryotic strain comprising the spores and the cultures incorporated within the spores of the heterokaryotic strain may be obtained.

Development of novel hybrid varieties via heteromixis comprises the controlled association and mating of two compatible cultures to obtain a novel heterokaryon culture. Homokaryons (='lines') are the preferred starting cultures for making matings as they have maximal ability to anastomose and achieve plasmogamy with other cultures. Heterokaryons may also be confronted but, especially when confronted with other heterokaryons, with commercially unreasonably low probabilities of a mating resulting in successful formation of a novel heterokaryon. Compatibility is determined by the genotype at the MAT locus; two homokaryons with the same MAT allele cannot establish a heterokaryon after anastomosis. In a defined mating program, homokaryotic lines are obtained and are associated in predetermined pairwise combinations. In one method, homokaryon pairs may be placed in close proximity on the surface of a nutrient agar medium in a petri dish and allowed to grow together (in a physical association), at which point anastomoses between the two cultures occur. A successful outcome is a mating. The novel hybrid heterokaryon may be obtained by transferring mycelium from the fusion zone of the dish. Such a paired mating method was used to develop hybrid heterokaryotic strains from lines obtained from strain B12998.

In contrast, Essentially Derived Varieties (EDVs) are most often derived directly from a single initial culture (e.g., strain); all such derivations produce EDVs. There is no universally accepted definition of an EDV; one example of a definition applicable to plant varieties is provided by the US Plant Variety Protection Act (revised edition, February 2006). The definition employed herein is congruent with the term as it is widely understood. 'Essential derivation' methods of obtaining cultures which are by definition consequently EDVs of a single initial culture of *A. bisporus* include somatic selection, tissue culture selection, single spore germination, multiple spore germination, selfing, repeated mating back to the initial culture, mutagenesis, and transformation, to provide some examples. DNA-mediated transformation of *A. bisporus* has been reported by Velcko, A. J. Jr., Kerrigan, R. W., MacDonald, L. A., Wach, M. P., Schlagnhaufer, C., and Romaine, C. P. 2004, Expression of novel genes in *Agaricus bisporus* using an *Agrobacterium*-mediated transformation technique. Mush. Sci. 16: 591-597, and references therein, herein incorporated by reference. Transformation may introduce a single new gene or allele into the genome of an initial culture.

EDVs are unambiguously recognizable by their genotype, which will be entirely or predominantly a subset that of the single initial culture. Percentages of the initial genotype that will be present in *Agaricus bisporus* EDVs range from almost 100% in the case of somatic selections, to 99.x % in the case of strains modified by DNA-mediated transformation, to 90-99.x % in the case of single or multiple spore selections or some mutagenesis, or even 100% with heterokaryotic internuclear reassociation of chromosomes in some instances, to an average of from about 75 to about 85% in the case of sibling-offspring matings (=selfing), to 75% on average in a first generation of backcrossing. Many methods of genotype determination, including methods described below, and others well known in the art, may be employed to determine the percentage of DNA of an initial culture that is present in another culture.

It will be understood that "derivation" does not include "descent by mating" and that "derivation" and "descent" are two completely different concepts not to be conflated. Further, an EDV must, axiomatically, as is well understood in the art, only be obtainable subsequent in time and in process execution to the initial variety or strain.

Genotypic fingerprints are descriptions of the genotype at defined loci, where the presence of characterized alleles is recorded. Such fingerprints provide powerful and effective techniques for recognizing clones and all types of EDVs of an initial strain, as well as for recognizing ancestry within outbred lineages. Many techniques are available for defining and characterizing loci and alleles in the genotype. The most detailed approach is provided by whole-genome sequencing (WGS), which allows for direct characterization and comparison of DNA sequences across the entire genome. Using this approach to generate robust genotypic fingerprints incorporating large numbers of marker loci, it is possible to establish the nature of the relationship between two strains, including strains related by genealogical descent over several generations. Sylvan America, Inc. has tracked genetic markers through four to six generations of its breeding pedigrees. If a sufficient number of rare markers are present in an initial strain or line, it will be possible to identify descent from an initial strain or line after several outbred generations without undue experimentation. In a hypothetical example, the mean expectation for genomic representation of an initial haploid line after 4 outbred generations is 3.1% in an F4 hybrid, which corresponds to ca. 1 Mb of the nuclear genomic DNA of *A. bisporus*. Based on Sylvan America's analyses, that amount of DNA from each of two unrelated strains of *A. bisporus* may typically contain from about 10,000 to about 20,000 single nucleotide polymorphisms (SNPs), any one of which may provide a distinguishing marker linking the F4 hybrid to the initial line. By using multiple independent markers, ancestors of a strain can be identified with a very high probability of success and with high confidence.

The advantages of the present invention over existing prior art relating to *Agaricus bisporus* mushrooms and cultures, which shall become apparent from the description which follows, are accomplished by the invention as hereinafter described and claimed.

One or more aspects of the present invention may be provided by an *Agaricus bisporus* mushroom culture B12998, the culture of the line B12998 having been deposited under the NRRL Accession Number 50902. In one embodiment, the culture may be that of strain B12998 itself. In other embodiments, the culture above may be an F1 hybrid *Agaricus bisporus* mushroom culture produced by mating a line obtained from the culture of the strain B12998 with a different *Agaricus bisporus* culture. Thus, it will be appreciated that, in one embodiment, a part of the culture of the strain B12998 above, and/or a part of an F1 hybrid strain having strain B12998 as at least one parent, may be selected from the group consisting of hyphae, spores, and cells and parts of cells, including, nuclei, mitochondria, cytoplasm, protoplasts, DNA, RNA, proteins, cell membranes and cell walls, each part being present in either the vegetative mycelium of the culture or in mushrooms produced by the culture, or both. In one or more embodiments, the part of the hybrid mushroom culture may be selected from the group consisting of DNA, RNA and proteins, wherein the DNA includes the same allelic characters that are present in strain 12998, wherein a culture of strain B12998 has been deposited under NRRL Accession Number 50902, and wherein said RNA and proteins have expressed sequence characters corresponding to and determined by the allelic characters of the DNA.

Further, in other embodiments, the culture of the strain B12998 above, and/or a culture of an F1 hybrid strain having strain B12998 as at least one parent, may be incorporated into products selected from mycelium, spawn, inoculum, casing inoculum, fresh mushrooms, processed mushrooms, mushroom extracts and fractions, mushroom pieces, and colonized substrates including grain, compost, and friable particulate matter. In other embodiments, the F1 hybrid mushroom culture of *Agaricus bisporus* above may be processed into one or more products selected from the group consisting of mycelium, spawn, inoculum, casing inoculum, fresh mushrooms, processed mushrooms, mushroom extracts and fractions, mushroom pieces, and colonized substrates including grain, compost, and friable particulate matter. In other embodiments, a mushroom may be produced by growing a crop of mushrooms from the culture of the strain B12998 above, and/or a from an F1 hybrid strain having strain B12998 as at least one parent. In further embodiments, a culture having at least one set of chromosomes comprising a set of alleles that are entirely or predominantly a subset of those of strain B12998, as detailed in Table V below or in other genotype tables presented in a co-pending US and PCT Applications entitled "Mushroom Line B129998-s39 and Methods and Uses Therefor" related to line B12998-s39, wherein the PCT application has been filed concurrently herewith and the US application was filed with the priority application, the disclosures of which are incorporated herein by reference, is produced. In yet further embodiments, an Essentially Derived Variety of the culture of strain B12998 is produced. In still other embodiments, an Essentially Derived Variety of an F1 hybrid mushroom culture above, having strain B12998 as at least one parent; is produced.

As noted in the definitions, the Essentially Derived Variety (EDV) has at least 75% of the genome or genotype that is present in the genome or genotype of the initial culture. As set forth in this invention, embodiments of the initial culture may include (a) strain B12998, (b) the F1 hybrid culture incorporating a line obtained from B12998, (c) the EDV of B12998 or of the line obtained from B12998, or (d) the EDV of the F1 hybrid culture incorporating the line from B12998, wherein a culture of the strain B12998 has been deposited under NRRL Accession Number 50902. In further embodiments, the EDV is a culture derived from (1) a single initial culture of strain B12998, (2) an Essentially Derived Variety of a single initial culture of strain B12998 or a line ontained from B12998, (3) the F1 hybrid of either (1) or (2), or (4) an EDV of (1), (2) or (3), wherein a culture of the line B12998-s39 has been deposited under NRRL Accession Number 50899.

One or more other aspects of the present invention may be provided by a process for introducing a desired trait into a culture of an initial *Agaricus bisporus* line. Such a process may be initiated by (1) mating the culture of a line to a second culture of *Agaricus bisporus* having the desired trait, to produce a hybrid. The process further proceeds by (2) obtaining an offspring that carries at least one gene that determine the desired trait from the hybrid produced above. The process further includes (3) mating the offspring of the hybrid with the culture of the initial line above to produce a new hybrid and (4) repeating the steps of (2) obtaining and (3) mating at least once to produce a subsequent hybrid. That is, step (4) may be repeated up to any of 1, 2, 3, 4, 5, 6, 7, 8, 9 and 10 times. In other embodiments, repeating steps (2) and (3) may occur more than 10 times. Upon completion of step (4), the process then provides (5) obtaining a homokaryotic line carrying at least one gene that determines the desired trait and comprises at least 75% of the alleles of the initial line at the sequence-characterized marker loci known for strain B12998 and consequently for lines obtained from strain B12998, for example as described in Table V below or in other genotype tables presented in a US application entitled "Mushroom Line B129998-s39 and Methods and Uses Therefor" filed concurrently herewith, from the subsequent hybrid of step (4). In one embodiment, the homokaryotic line obtained may comprise 80% of the alleles of the initial line at the known loci for strain B12998 and for lines obtained from B12998, for example the sequence-characterized marker loci described in Table V below or in other genotype tables presented in a US application entitled "Mushroom Line B129998-s39 and Methods and Uses Therefor". In other embodiments, the homokaryotic line obtained may comprise 85%, 90%, 95%, 96%, 97%, 98%, 99% or may be comprise essentially 100% of the alleles of the initial line at the known loci for strain B12998 and for lines obtained from B12998, for example the sequence-characterized marker loci described in Table V below or in other genotype tables presented in a US application entitled "Mushroom Line B129998-s39 and Methods and Uses Therefor."

Still one or more other aspects of the present invention may be provided by a process of producing a hybrid mushroom culture. The process includes mating a first mushroom culture with a second mushroom culture, wherein at least one of the first and second mushroom cultures is an *Agaricus bisporus* culture having all of the physiological and morphological characteristics of a line obtained from strain B12998, wherein the culture of said strain B12998 was deposited under the NRRL Accession Number 50902. In one embodiment, a hybrid culture is produced by this process. In another embodiment, a hybrid mushroom, or its parts, may be produced by growing a crop of mushrooms from the hybrid culture above. In yet another embodiment, a part of the hybrid culture above may be selected from the group consisting of hyphae, mushrooms, spores, cells, nuclei, mitochondria, cytoplasm, protoplasts, DNA, RNA, proteins; cell membranes and cell walls. In other embodiments, the hybrid culture of *Agaricus bisporus* above may be incorporated into one or more products selected from the group consisting of mycelium, spawn, inoculum, casing inoculum, fresh mushrooms, processed mushrooms, mushroom extracts and fractions, mushroom pieces, and colonized substrates including grain, compost, and friable particulate matter.

Still one or more other aspects of the present invention may be provided by an *Agaricus bisporus* culture having the essential physiological and morphological characteristics of strain B12998, wherein the culture of said strain B12998 was deposited under the NRRL Accession Number 50902. In one embodiment, the culture may have all of the physiological and morphological characteristics of strain B12998 wherein a culture of strain B12998 has been deposited under the NRRL Accession Number 50902. In other embodiments, the culture may include a marker profile in accordance with the marker profile of line B12998 shown in Table V below or in other genotype tables presented in a US application entitled "Mushroom Line B129998-s39 and Methods and Uses Therefor", filed concurrently herewith. In one or more embodiments, the culture above provides a cell. In one or more embodiments, the cell above may include a marker profile in accordance with the profile of strain B12998 shown in Table V below or in other genotype tables presented in a US application entitled "Mushroom Line B129998-s39 and Methods and Uses Therefor" filed concurrently herewith. In other embodiments, a spore may comprise the cell above. In other embodiments, the hybrid culture above may be further defined as having a genome including a single locus trait conversion. In further embodiments, the locus above may be selected from the group consisting of a dominant allele and a recessive allele. In one or more other embodiments, the locus above may confer a trait selected from the group consisting of mushroom size, mushroom shape, mushroom cap roundness, mushroom flesh thickness, mushroom color, mushroom surface texture, mushroom cap smoothness, tissue density, tissue firmness, delayed maturation, basidial spore number greater than two, sporelessness, increased dry matter content, increased shelf life, reduced brusing, increased yield, altered distribution of yield over time, decreased spawn to pick interval, resistance to infection by symptoms of or transmission of bacterial, viral or fungal disease or diseases, insect resistance, nematode resistance, ease of crop management, suitability of crop for mechanical harvesting, canning and/or processing, desired behavioral response to environmental conditions, to stressors, to nutrient substrate composition, to seasonal influences, and to farming practices.

Still one or more other aspects of the present invention may be provided by a method of producing a mushroom culture. The method includes (a) growing a progeny culture produced by mating a first culture having the essential physiological and morphological characteristics of strain B12998, wherein the culture of said strain B12998 was deposited under the NRRL Accession Number 50902, with a second *Agaricus bisporus* culture; (b) mating the progeny culture with itself or a different culture to produce a progeny culture of a subsequent generation; (c) growing a progeny culture of a subsequent generation and mating the progeny culture of a subsequent generation with itself or a different culture; and (d) repeating steps (b) and (c) for an additional 0, 1, 2, 3, 4 or 5 (i.e., 0-5) generations to produce a mushroom culture. In one embodiment, the first culture has all of the physiological and morphological characteristics of strain B12998. In another embodiment, the method includes mating a culture of strain B12998 with a culture of a second homokaryotic line. In still other embodiments, the produced mushroom culture above is an inbred culture. In one or more other embodiments, the method above may further include the step of mating the inbred culture with a second, distinct culture to produce an F1 hybrid culture.

Yet one or more other aspects of the present invention may be provided by a method for developing a second culture in a mushroom strain development program. Such a method includes applying mushroom strain development techniques to a first mushroom culture, or parts thereof, wherein the first mushroom culture is a culture having the essential physiological and morphological characteristics of strain B12998, wherein the culture of said strain B12998 was deposited under the NRRL Accession Number 50902. In one embodiment, the culture is that of strain B12998 itself. In another embodiment, the culture has all of the physiological and morphological characteristics of strain B12998. It is the application of the mushroom strain development techniques that results in the development of the second culture. Such known mushroom strain development techniques are selected from the group consisting of inbreeding, outbreeding, selfing, introgressive trait conversions, essential derivation, pedigree-assisted breeding, marker assisted selection, and transformation.

Finally, another aspect of the present invention may be provided by a method of mushroom strain development. This method includes obtaining a molecular marker profile of *Agaricus bisporus* mushroom strain B12998, a culture of which was deposited under the NRRL Accession Number 50902. Another step of the method includes obtaining an F1 hybrid culture, for which the deposited mushroom culture of the *Agaricus bisporus* mushroom strain B12998 is a parent. Once the F1 hybrid culture is obtained, a further step of mating a culture obtained from the F1 hybrid culture with a different mushroom culture is employed. Once this is done, the selection of progeny that possess characteristics of the molecular marker profile of strain B12998 as above may be conducted to complete the method using known techniques.

Yet other embodiments of the invention are provided by using, in place of strain B12998, in the embodiments described above, a hybrid strain obtained from the mating of any of the following combinations of two strains, including strains from their corresponding derived lineage groups: an OW strain to BP-1, an SW strain to BP-1, an HW strain to BP-1, or an experimental BW strain to BP-1.

DETAILED DESCRIPTION OF THE INVENTION

Initially, in order to provide clear and consistent understanding of the specification and claims, including the scope to be given such terms, the following definitions are provided.

Allele: A heritable unit of the genome at a defined locus, ultimately identified by its DNA sequence (or by other means); in a genotype, an allelic character.

Amphithallism: A reproductive syndrome in which heteromixis and intramixis are both active.

Anastomosis: Fusion of two or more hyphae that achieves cytoplasmic continuity.

Basidiomycete: A monophyletic group of fungi producing meiospores on basidia; a member of a corresponding subdivision of Fungi such as the Basidiomycetales or Basidiomycotina.

Basidium: The meiosporangial cell, in which karyogamy and meiosis occur, and upon which the basidiospores are formed.

Bioefficiency: For mushroom crops, the net fresh weight of the harvested crop divided by the dry weight of the compost substrate at the time of spawning, for any given sampled crop area or compost weight.

Breeding: Development of strains, lines or varieties using methods that emphasize sexual mating; see Descent.

BW-type hybrid strain: A category of initial strains (and their derived lineage groups) obtained by hybridization of one white-capped parent line and one brown-capped parent line (i.e., the two lines carry alleles determining white or brown cap color, respectively, at the PPC1 locus), exemplified by SC-600, Broncoh, 4x29, J10259, J10261, J10263, and B12998; BW-type hybrid, BW strain, BW.

Cap: Pileus; part of the mushroom, the gill-bearing structure.

Cap Roundness: Strictly, a ratio of the maximum distance between the uppermost and lowermost parts of the cap, divided by the maximum distance across the cap, measured on a longitudinally bisected mushroom; typically averaged over many specimens; subjectively, a 'rounded' property of the shape of the cap.

Carrier substrate: A medium having both nutritional and physical properties suitable for achieving both growth and dispersal of a culture.

Casing layer, casing: A layer of non-nutritive material such as peat or soil that is applied to the upper surface of a mass of colonized compost in order to permit development of the mushroom crop.

Casing inoculum (CI): A formulation of inoculum material incorporating a mushroom culture, typically of a defined heterokaryotic strain, suitable for mixing into the casing layer.

Cloning: Somatic propagation without selection.

Combining ability: The capacity of an individual to transmit traits or superior performance to its offspring (known and available methods of assessment vary by trait).

Compatibility: See heterokaryon compatibility.

Culture: The tangible living organism; the organism propagated on various growth media and substrates; one instance of one physical strain, line, homokaryon or heterokaryon; the sum of all of the parts of the culture, including hyphae, mushrooms, spores, cells, protoplasts, nuclei, mitochondria, cytoplasm, DNA, RNA, and proteins, cell membranes and cell walls.

Derivation: Development of a strain or culture from a single initial strain, or predominantly from a single initial strain, in contrast to descent via sexual mating between two parental strains; see Essentially Derived Variety (EDV).

Derived lineage group: An initial strain or variety and the set of EDVs derived from that single initial strain or variety.

Descent: The production of offspring from two parents, and/or four grandparents, and/or additional progenitors, via sexual mating; in contrast to derivation from a single initial strain.

Diploid: Having two haploid chromosomal complements within a single nuclear envelope.

Essential derivation: A process by which an Essentially Derived Variety is obtained from an initial variety or strain or from an EDV of an initial variety or strain; modification of an initial culture using methods including somatic selection, tissue culture selection, selfing including intramictic reproduction via single spores and multiple spores and mating of sibling offspring lines, back-mating to the initial variety, or mutagenesis and/or genetic transformation of the initial variety to produce a distinct culture in which the genotype of the resulting culture is predominantly that of the initial culture.

Essentially Derived Variety (EDV): (Note: EDV definitions for example, as applied to plants in the US PVPA, incorporate elements of (1) relatedness, (2) methods of derivation, (3) and empirical tests.) A variety having 75% to 99.99999% genetic identity with an initial strain or variety, or to 100% in a heterokaryon with internuclear reassociation of chromosomes. In general, a variety that is entirely or predominantly derived from an initial variety or from an EDV of an initial variety, and which conforms to specified or "essential" characteristics of the initial variety except for distinguishing differences resulting from the act of derivation, is an EDV of the initial variety. In the art of mushroom strain development, a strain or culture predominantly or entirely derived from a single initial strain or culture, thus having most or all, but at least 75%, of its genome or genotype present in the genome or genotype of the initial strain or culture; a strain or culture obtained from an initial strain or culture by somatic selection, tissue culture selection, selfing including mating of sibling offspring lines and intramictic reproduction via single or multiple spores, back-mating to the initial strain or culture, or mutagenesis and/or genetic transformation of the initial strain or culture; a strain or culture reconstituted from neohaplonts derived from an initial strain or culture, whether or not the haploid lines have been passed into or out of other heterokaryons; a strain or culture with the same essential phenotype as that of an initial strain or culture; in contrast to descent (via sexual mating between two parental strains).

Flesh Thickness: A ratio of the maximum distance between the top of the stem and the uppermost part of the cap, divided by the maximum distance across the cap, measured on a longitudinally bisected mushroom; typically averaged over many specimens; subjectively called 'meatiness'.

Flush: A period of mushroom production within a cropping cycle, separated by intervals of non-production; the term flush encompasses the terms 'break' and 'wave' and can be read as either of those terms.

Fungus: An organism classified as a member of the Kingdom Fungi.

Genealogical descent: Descent from progenitors, including parents, over a limited number (e.g., 10 or fewer) of typically outcrossed generations; in contrast to derivation from a single initial strain.

Genotypic fingerprint: A description of the genotype at a defined set of marker loci; the known genotype.

Gill: Lamella; part of the mushroom, the hymenophore- and basidium-bearing structure.

Haploid: Having only a single complement of nuclear chromosomes; see homokaryon.

Heteroallelic: Having two different alleles at a locus; analogous to heterozygous.

Heteroallelism: Differences between homologous chromosomes in a heterokaryotic genotype; analogous to heterozygosity.

Heterokaryon: As a term of art this refers to a sexual heterokaryon: a culture which has two complementary (i.e., necessarily heteroallelic at the MAT locus) types of haploid nuclei in a common cytoplasm, and is thus functionally and physiologically analogous to a diploid individual (but cytogenetically represented as N+N rather than 2N), and which is potentially reproductively competent, and which exhibits self/non-self incompatibility reactions with other heterokaryons; also called a strain or stock in the breeding context.

Heterokaryon compatibility: The absence of antagonism observed during physical proximity or contact between two heterokaryons that are not genetically identical; see Heterokaryon Incompatibility.

Heterokaryon incompatibility: The phenomenon of antagonism observed during physical proximity or contact between two heterokaryons that are not genetically identical; a multilocus self/non-self recognition system that operates in basidiomycete heterokaryons.

Heterokaryotic: Having the character of a heterokaryon.

Heteromixis: Life cycle involving mating between two different non-sibling haploid individuals or gametes; outbreeding.

Homoallelic: Having not more than one allele at a locus. The equivalent term in a diploid organism is 'homozygous'. Haploid lines are by definition entirely homoallelic at all non-duplicated loci.

Homokaryon: A haploid culture with a single type (or somatic lineage) of haploid nucleus (cytogenetically represented as N), and which is ordinarily reproductively incompetent, and which does not exhibit typical self/non-self incompatibility reactions with heterokaryons, and which may function as a gamete in sexually complementary anastomoses; a 'line' which, as with an inbred plant line, transmits a uniform genotype to offspring; a predominantly homoallelic line that mates well and fruits poorly is a putative homokaryon for strain development purposes; see discussion below.

Homokaryotic: Having the character of a homokaryon; haploid.

HW-type hybrid strain: A category of strains obtained by hybridization of parent strains, and having a white cap color, also comprising any derived lineage groups that include an initial strain which is also an HW type hybrid strain and its EDVs, exemplified by strains U1, A-15, S-130, AS 2796, AS3003, B7970, J9277, B9798, J10102, J10117, J10165, J11500, and others; Hybrid White strain, HW-type hybrid, HW strain, HW.

Hybrid: Of biparental origin, usually applied to heterokaryotic strains and cultures produced in controlled matings.

Hybridizing: Physical association, for example on a petri dish containing a sterile agar-based nutrient medium, of two cultures, usually homokaryons, in an attempt to achieve anastomosis, plasmogamy, and formation of a sexual heterokaryon (=mating); succeeding in the foregoing.

Hyphae: Threadlike elements of mycelium, composed of cell-like compartments.

Inbreeding: Matings that include sibling-line matings, back-matings to parent lines or strains, and intramixis; reproduction involving parents that are genetically related.

Incompatibility: See heterokaryon incompatibility.

Inoculum: A culture in a form that permits transmission and propagation of the culture, for example onto new media; specialized commercial types of inoculum include spawn and CI; plural: inocula.

Intramixis: A uniparental sexual life cycle involving formation of a complementary 'mated' pair of postmeiotic nuclei within the basidium or individual spore.

Introgressive trait conversion: mating offspring of a hybrid to a parent line or strain such that a desired trait from one strain is introduced into a predominating genetic background of the other parent line or strain.

Lamella: see 'gill'.

Line: A culture used in matings to produce a hybrid strain; ordinarily a homokaryon which is thus homoallelic, otherwise a non-heterokaryotic (non-NSNPP) culture which is highly homoallelic; practically, a functionally homokaryotic and entirely or predominantly homoallelic culture; analogous in plant breeding to an inbred line which is predominantly or entirely homozygous.

Lineage group: see 'derived lineage group'. The set of EDVs derived from a single initial strain or variety.

Locus: A defined contiguous part of the genome, homologous although often varying among different genotypes; plural: loci.

Marker assisted selection: Using linked genetic markers including molecular markers to track trait-determining loci of interest among offspring and through pedigrees.

MAT: The mating-type locus, which determines sexual compatibility and the heterokaryotic state.

Mating: The sexual union of two cultures via anastomosis and plasmogamy;

methods of obtaining matings between mushroom cultures are well known in the art.

Mycelium: The vegetative body or thallus of the mushroom organism, comprised of threadlike hyphae.

Mushroom: The reproductive structure of an agaric fungus; an agaric; a cultivated food product of the same name.

Neohaplont: A haploid culture or line obtained by physically deheterokaryotizing (reducing to haploid components) a heterokaryon; a somatically obtained homokaryon.

OFB: Old-Fashioned Brown type strain; a traditional cultivar derived lineage group originating from a single initial wild strain in Europe, and also including its EDVs, exemplified by strains SB-65, SB-295, RWK_2042; OFB strain, OFB-type strain.

Offspring: Descendents, for example of a parent heterokaryon, within a single generation; most often used to describe cultures obtained from spores from a mushroom of a strain.

Outbreeding: Mating among unrelated or distantly related individuals.

OW-type strain: A category of cultivar strains traditionally called 'Off-white' strains, comprising an initial strain and its derived lineage group, exemplified by strain Somycel 76; OW strain, OW.

Parent: An immediate progenitor of an individual; a parent strain is a heterokaryon; a parent line is a homokaryon; a heterokaryon may be the parent of an F1 heterokaryon via an intermediate parent line.

Pedigree-assisted breeding: The use of genealogical information to identify desirable combinations of lines in controlled mating programs.

Phenotype: Observable characteristics of a strain or line as expressed and manifested in an environment.

Plasmogamy: Establishment, via anastomosis, of cytoplasmic continuity leading to the formation of a sexual heterokaryon.

Progenitor: Ancestor, including parent (the direct progenitor).

Selfing: Mating among sibling lines; also intramixis.

Somatic: Of the vegetative mycelium.

Spawn: A mushroom culture, typically a pure culture of a heterokaryon, typically on a sterile substrate which is friable and dispersible particulate matter, in some instances cereal grain; commercial inoculum for compost; reference to spawn includes reference to the culture on a substrate.

Spore: Part of the mushroom, the reproductive propagule.

Stem: Stipe; part of the mushroom, the cap-supporting structure.

Sterile Growth Media: Nutrient media, sterilized by autoclaving or other methods, that support the growth of the organism; examples include agar-based solid nutrient media such as Potato Dextrose Agar (PDA), nutrient broth, and many other materials.

Stipe: see 'stem'.

Strain: A heterokaryon with defined characteristics or a specific identity or ancestry; equivalent to a variety.

SW-type strain: A category of cultivar strains traditionally called 'Smooth-white' strains, comprising an initial strain and its derived lineage group, exemplified by strain Somycel 53; SW strain, SW.

Tissue culture: A de-differentiated vegetative mycelium obtained from a differentiated tissue of the mushroom.

Trait conversion: Selective introduction of the genetic determinants of one (a single-locus conversion) or more desirable traits into the genetic background of an initial strain while retaining most of the genetic background of the initial strain. See 'Introgressive trait conversion' and 'Transformation'.

Transformation: A process by which the genetic material carried by an individual cell is altered by the incorporation of foreign (exogenous) DNA into its genome; a method of obtaining a trait conversion including a single-locus conversion.

Virus-breaking: Using multiple incompatible strains, i.e. strains exhibiting heterokaryon incompatibility, successively in a program of planned strain rotation within a mushroom production facility to reduce the transmission of virus from on-site virus reservoirs into newly planted crops.

Yield: The net fresh weight of the harvest crop, normally expressed in pounds per square foot.

Yield pattern: The distribution of yield within each flush and among all flushes; influences size, quality, picking costs, and relative disease pressure on the crop and product.

With respect to the definition of homokaryon above, it is noted that homokaryons and homoallelic lines are subject to technical and practical considerations: A homokaryon in classical terms is a haploid culture which is axiomatically entirely homoallelic. In practical terms, for fungal strain development purposes, the definition is broadened somewhat to accommodate both technical limitations and cytological variation, by treating all predominately homoallelic lines as homokaryons. Technical limitations include the fact that genomes contain duplicated DNA regions including repeated elements such as transposons, and may also include large duplications of chromosomal segments due to historical translocation events. Two different *A. bisporus* genomes sequenced by the Joint Genome Institute, a U.S. federal facility, differ in estimated length by 4.4%, and in gene numbers by 8.2%, suggesting a considerable amount of DNA duplication or rearrangement within different strains of the species. No presently available genome of *A. bisporus* can completely account for the physical arrangement of such elements and translocations, and so the assembled genome sequences of haploid lines may have regions that appear to be heteroallelic using currently available genotyping methods. Cytologically, a homokaryotic offspring will ordinarily be a spore that receives one haploid, postmeiotic nucleus. However, a spore receiving two third-division nuclei from the basidium will be genetically equivalent to a homokaryon. A spore receiving two second-division 'sister' postmeiotic nuclei will be a functional homokaryon even though some distal 'islands' of heteroallelism may be present due to crossovers during meiosis. Also, a meiosis that has an asymmetrical separation of homologues can produce an aneuploid, functionally homokaryotic spore in which an extra chromosome, producing a region of heteroallelism, is present. All of these cultures are highly homoallelic and all function as homokaryons. Technological limitations make it impractical to distinguish among such cultures, and also to rule out DNA segment duplication as an explanation for limited, isolated regions of the genome sequence assembly that appear to be heteroallelic. Therefore, in the present application, the use of the term 'homoallelic' to characterize a line includes entirely or predominately homoallelic lines, and cultures described in this way are functional homokaryons, are putatively homokaryotic, and are all defined as homokaryons in the present application.

Now, with respect to the invention and as noted hereinabove, the present invention relates to a heterokaryotic strain, and more specifically, a strain of *Agaricus bisporus* designated B12998, and methods for using the strain designated B12998. A culture of the strain designated B12998 has been deposited with the Agricultural Research Services Culture Collection (NRRL) 1815 North University Street, Peoria, Ill. 61604 USA ("NRRL") as Accession No. 50902.

Strain B12998 and lines obtained from strain B12998 can be used to produce hybrid cultures with desirable productivity, timing, appearance, and other agronomic traits as is required of successful commercial mushroom strains, while also providing more diversified, non-cultivar germplasm. Lines obtained from B12998 have been found to have advantageous genotypes for mating to produce commercially useful hybrid strains. Two useful stocks have contributed to the genome of hybrid strain B12998 and its offspring lines. One is the traditional white European stock designated Somycel 76, (NRRL Accession No. 50903) widely cultivated during the twentieth century. The other is a wild brown American stock designated BP-1 (ATCC Accession No. PTA-6903), obtained by R. W. Kerrigan circa 1990. In combination, the diverse genetic contributions of these two stocks, as present among hybrid strain B12998 and homokaryotic lines obtained from the hybrid strain B12998, were observed to have combined in various lines to produce spores and, from them, superior lines with excellent combining abilities in matings. It was further observed that other hybrid strains having BP-1 and OW parents in common with B12998, and also yet other hybrid strains having BP-1 as one parent and an SW, HW, or experimental BW strain as a second parent, also produce spores from which lines, which may have useful and desirable properties in mushroom strain development programs, may be obtained.

The lines obtained from strain B12998 are haploid and thus are entirely homoallelic (although some limited regions of duplicated DNA may be present in their genomes). The lines have shown uniformity and stability in culture. The lines have been increased by transfer of pure inocula into larger volumes of sterile culture media. No variant traits have been observed or are expected in lines obtained from strain B12998.

Mushroom cultures are most reliably identified by their genotypes, in part because successful cultivar strains are required by the market to conform to a narrow phenotypic range. The genotype can be characterized through a genetic marker profile, which can identify isolates (subcultures) of the same line, strain or variety, or a related variety including a variety derived entirely from an initial variety (i.e., an Essentially Derived Variety), or can be used to determine or validate a pedigree.

Means of obtaining genetic marker profiles using diverse techniques including whole genome sequencing are well known in the art. The whole genomic sequence of several strains and lines have been obtained by Sylvan America, Inc., or from other sources, and consequently, many differences that distinguish between these strains and lines are known to the Assignee with certainty. Typically, Sylvan has observed that between 300,000 and 700,000 marker differences may be reported by software-enabled analysis to distinguish between pairs of *A. bisporus* strains. As an example, a brief excerpt of the genotypes of several lines and strains at six sequence-characterized marker loci is provided in Table V.

TABLE V

Alleles at 6 marker loci in cultures of interest:

| Culture: | p1n150/Mat | ITS | MFPC-1-ELF | AN | AS | FF | % WGS |
|---|---|---|---|---|---|---|---|
| BP-1 | 2/5 | I1/I1 | E4/E4 | N3/N3 | SA/SB | FF2/FF3 | ca. 50% |
| BP-1-s53 | 5 | I1 | E4 | N3 | SA | FF2 | est. 25% |
| Somycel 76/OW | 1T/3 | I1/x | E1/x | N1/x | SD/x | FF1/x | est. 75% |
| So76-s39 | 3 | [I1 or I3] | [E1 or x] | [N1 or x] | [SD or x] | [FF1 or x] | ca. 50% |
| H97/OWNC | 1T | I1 | E1 | N1 | SD | FF1 | 100% |
| B12998 | 3/5 | I1/I1 | E1/E4 | N3/x | SC/x | FF1/FF3 | ca. 50% |
| B12998-s39 | 5 | I1 | E4 | N3 | SC | FF3 | ca. 100% |
| B14528 | 2/5 | I1/I2 | E3/E4 | N3/N4 | SC/SD | FF1/FF3 | ca. 100% |
| Somycel 53/SW | 2/3 | I2/x | E2/x | N2/x | SB/SC | FF2/x | est. 75% |
| So53-H39/SWNC | 2 | I2 | E2 | N2 | SC | FF2 | ca. 100% |
| U1 lineage group | 1T/2 | I1/I2 | E1/E2 | N1/N2 | SC/SD | FF1/FF2 | ca. 100% |
| OFB lineage group | 1T/3* | I1/I3 | E3/E6 | N4/N4 | SC/SD | FF1/FF2 | ca. 100% |
| PTA-6877 | 1T/2 | I1/I2 | E2/E3 | N2/N4 | SD/SD | FF1/FF1 | ca. 50% |
| 28C, [Heirloom] | 1T/5 | I1/I1 | E3/E4 | N2/N3 | SA/SD | FF1/FF3 | ca. 100% |
| 28B, [Braun] | 1T/5 | I1/I1 | E3/E4 | N2/N3 | SB/SD | FF1/FF4 | [<50%] |
| SC-600 | 1T/2 | [I1 or I3/x] | [E3 or E6/x] | N4/x | [SC or SD]/x | [FF1 or FF2]/x | [ca. 50%] |
| J10263 | 1T/2 | I1/[I1 or I3] | [E3 or E6/E2 or x] | N4/x | SD/x | [FF1 or FF2]/x | [<50%] |
| J453-s7 | 2 | I2 | [E2 or x] | x | x | x | |
| 56B-4186 | 1T | [I1 or I3] | [E3 or E6] | N4 | SD | [FF1 or FF2] | [<50%] |

Descriptions of the six sequence-characterized markers and their alleles are provided in the co-owned U.S. patent application Ser. No. 14/169,658, filed Jan. 31, 2014 and in the concurrently filed patent application entitled "Hybrid Mushroom Strain B14528 and Descendants Thereof," the disclosures of both of which are incorporated by reference.

The "p1n150-3G-2" marker is a refinement of the p1n150 marker reported on Chromosome 1 by Kerrigan, R. W., et al. "Meiotic behavior and linkage relationships in the secondarily homothallic fungus *Agaricus bisporus*." *Genetics* 133, 225-236 (1993), incorporated herein by reference, and shown to be linked to the MAT (mating type) locus by Xu et al., "Localization of the mating type gene in *Agaricus bisporus*." *App. Env. Microbiol.* 59(9): 3044-3049 (1993), incorporated herein by reference, and has also been used in other published studies. While several different primers can be and have been used to amplify segments of DNA in which the p1n150-3G-2 marker is present and from which it can be sequenced, digested, electrophoretically characterized, or otherwise analyzed, the primer sequences employed in the present invention for the development of the diiclosed data are: Forward: 5'-aggcryccatcttcasc-3' (SEQ. ID NO. 1); Reverse: 5'-gttcgacgacggactgc-3' (SEQ. ID NO. 2), with 35 PCR cycles, 56C anneal temperature, 1 min. extension time.

The "ITS" marker has been adopted as the official 'barcode' sequence for all fungi (Schoch et al., Fungal Barcoding Consortium, "Nuclear ribosomal internal transcribed spacer (ITS) region as a universal DNA barcode marker for Fungi." Proc. Nat. Acad. Sci. www.pnas.org/cgi/content/short/1117018109 (2012)), incorporated herein by reference, and has been used in innumerable publications, including Morin et al., "Genome sequence of the button mushroom *Agaricus bisporus* reveals mechanisms governing adaptation to a humic-rich ecological niche." Proc. Nat'l Acad. Sci. USA 109: 17501-17506 (2012), incorporated herein by reference, on the complete *A. bisporus* genome sequence. White et al. (1990), Amplification and direct sequencing of fungal ribosomal RNA genes for phylogenetics. In: PCR Protocols: a guide to methods and applications. (Innis MA, Gelfand DH, Sninsky JJ, White TJ, eds). Academic Press, New York, USA: 315-322., published many primer sequences for the ITS marker, of which the inventors use primers ITS1: 5'-tccgtaggtgaacctgcgg-3' (SEQ. ID NO. 3) and ITS4: 5'-tcctccgcttattgatatgc-3' (SEQ. ID. NO. 4), with 35 PCR cycles, 56C anneal temperature, 1 min. extension time.

The MFPC-1-ELF marker is derived from a sequence mapped by Marie Foulongne-Oriol et al., "An expanded genetic linkage map of an intervarietal *Agaricus bisporus* var. *bisporus*—*A. bisporus* var. *burnettii* hybrid based on AFLP, SSR and CAPS markers sheds light on the recombination behaviour of the species." *Fungal Genetics and Biology* 47: 226-236 (2010), incorporated herein by reference, that is linked to the PPC-1 locus described by Callac et al., "Evidence for PPC1, a determinant of the pilei-pellis color of *Agaricus bisporus* fruit bodies. *Fungal Genet. Biol.* 23, 181-188 (1998), incorporated by reference. An equivalent linked marker has been used as described in Loftus et al., "Use of SCAR marker for cap color in *Agaricus bisporus* breeding programs." *Mush. Sci.* 15, 201-205 (2000). While several different primers can be and have been used to amplify segments of DNA in which the MFPC-1-ELF marker is present and from which it can be sequenced, digested, electrophoretically characterized, or otherwise analyzed, the primer sequences employed by the inventors for the development of the disclosed data are: Forward: 5'-aytcrcaamaacataccttcaac-3' (SEQ. ID. NO. 5); reverse: 5'-cattcggcgattttctca-3' (SEQ. ID NO. 6), with 35 PCR cycles, 55C anneal temperature, 0.5 min. extension time.

The AN, AS, and FF markers were designed from sequences obtained from PCR products produced by the use of primers disclosed by Robles et al., U.S. Pat. No. 7,608,760, and/or from contiguous or overlapping genome sequences, to improve upon the performance, reliability, and consistency of results, as compared to the markers as originally described; they are genotypically and genomically equivalent. While several different primers can be and have been used to amplify segments of DNA in which either the AN, AS, or FF marker is present and from which it can be sequenced, digested, electrophoretically characterized, or otherwise analyzed, the primer sequences employed by the inventors for the development of the disclosed data are: for AN: Forward: 5'-gacgatgcgggactggtggat-3' (SEQ. ID NO. 7); Reverse: 5'-ggtctggcctacrggagtgttgt-3' (SEQ. ID NO. 8), with 35 PCR cycles, 64C anneal temperature, 2 min. extension time; for AS: Forward: 5'-ccgccagcacaaggaatcaaatg-3' (SEQ. ID NO. 9); Reverse: 5'-tcagtcggccctcaaaacagtcg-3' (SEQ. ID NO. 10), with 35 PCR cycles, 64C anneal temperature, 2 min. extension time; and for FF: Forward: 5'-tcgggtggttgcaactgaaaag-3' (SEQ. ID NO. 11); Reverse: ttccttccgccttaattgtttct (SEQ. ID NO. 12), with 35 PCR cycles, 64C anneal temperature, 2 min. extension time.

The IUPAC nucleotide and ambiguity codes were used to represent the polymorphisms in the DNA marker sequences. The identity of each marker locus was further specified by the scaffold and SNP position information derived from the H97 V2.0 reference genome sequence published by the U.S. Department of Energy Joint Genome Institute (Morin et al. 2012). Distinctions between the genotypes of these strains and lines are evident. Most of the genotypes reported above are known with certainty or else within relatively narrow limits. Alleles which are undetermined at this time are represented with an 'x'. Table V also provides information on how much of the nuclear genome sequence of each line or strain is known to Sylvan America, Inc. at this time. Many other distinguishing markers are known to Sylvan America, Inc. to occur within the overall genotype of each line or strain. Those and additional markers are available for all genotyping purposes described herein. Known markers number several hundred thousand and are documented in exhaustive tables prepared by Sylvan America, however they are too numerous to list in their entirety in the present application.

It will be appreciated that the DNA of the present invention is that which includes the same allelic characters that are present in strain B12998. Thus, regardless of the process of producing the DNA from strain B12998, it is identifiable DNA because it includes the same allelic characters as those present in strain B12998 that is claimed.

With respect to the RNA and proteins set forth in the present invention, it is understood in the art that the central dogma of molecular biology, fully proven experimentally, and as explained on the National Institutes of Health website, at www.ncbi.nlm.nih.gov/Class/MLACourse/Modules/MolBioReview/centraldogma.html, (published as of February 2014) teaches that RNA is transcribed directly from the nuclear and mitochondrial DNA such that information present in the DNA sequence is incorporated in the corresponding RNA sequence. Similarly, the amino acid sequence of proteins is translated directly from RNA sequences such that the information present in the sequence of the protein is directly determined by the RNA sequence, and, ultimately, by the DNA sequence. Together, transcription and/or translation of a DNA gene sequence are called "expression" or "gene expression". Distinguishing characters of a DNA sequence are reflected in corresponding unique sequences of the expressed RNA and protein sequences.

Lines of B12998 can be identified through their molecular marker profiles as can be understood from Table V above or in other genotype tables presented in a US application entitled "Mushroom Line B129998-s39 and Methods and Uses Therefor" filed concurrently herewith and incorporated herein by reference. A culture or product incorporating a genetic marker profile of a line obtained from B12998 is an embodiment of the invention. Another embodiment of this invention is an *Agaricus bisporus* line or its parts comprising the same known alleles, for example among those listed in tables including Table V, as a line obtained from B12998 for at least 75% of the loci characterized for said line. In other embodiments, said line or its parts comprises the same known alleles as the initial line obtained from B12998 for at least 80%, 85%, 90%, 95%, 96%, 97%, 98%, 99% or essentially 100% of the loci known, for example among those listed in tables including Table V.

A cell comprising the same known alleles as a cell of a line obtained from strain B12998 for at least 75% of those loci, for example those listed in tables including Table V above or in other genotype tables presented in a US application entitled "Mushroom Line B129998-s39 and Methods and Uses Therefor", is also an embodiment of this invention. In other embodiments, cells comprising the same alleles as a cell of a line obtained from strain B12998 for at least 80%, 85%, 90%, 95%, 96%, 97%, 98%, 99% or essentially 100% of the loci listed in tables including Table V above or in other genotype tables presented in a US application entitled "Mushroom Line B129998-s39 and Methods and Uses Therefor" filed concurrently herewith, are provided. Also encompassed within the scope of the invention are cultures substantially benefiting from the use of a line obtained from strain B12998 in their development, such as hybrid offspring having a line obtained from strain B12998 as a parent, and a line obtained from strain B12998 having a trait introduced through introgressive matings of offspring back to the line obtained from strain B12998, or through transformation. Similarly, an embodiment of this invention is an *Agaricus bisporus* heterokaryon comprising at least one allele per locus that is the same allele as is present in the line obtained from strain B12998 for at least 75% of the marker loci known. In other embodiments, heterokaryons comprising at least one allele per locus that is the same allele as is present in a line obtained from strain B12998 for at least 80%, 85%, 90%, 95%, 96%, 97%, 98%, 99% or essentially 100% of the marker loci known, are provided. More particularly, the heterokaryon may be a hybrid descendent of a line obtained from strain B12998.

Mushroom-forming fungi exhibit an alternation of generations, from heterokaryotic (N+N, with two haploid nuclei, functionally like the 2N diploid state) to homokaryotic (1N) and further upon mating to become heterokaryotic again. In most eukaryotes, a parent is conventionally considered to be either diploid or heterokaryotic. The haploid 'generation' is often, but not always, termed a gamete (e.g., pollen, sperm). In fungi, which are microorganisms, the haploid generation can live and grow indefinitely and independently, for example in laboratory cell culture; while these haploid homokaryons function as gametes in matings, they are equivalent to inbred lines (e.g., of plants) and are more easily referred to as parents (of hybrids). Herein, the term 'parent' refers to the culture that is a, or the, direct progenitor of another culture within the alternating generations of the sexual lifecycle. The term 'line' refers more narrowly to a haploid (N) homoallelic culture within the lifecycle. The N+N heterokaryon resulting from a mating, or comprising a breeding stock, or comprising a culture used to produce a crop of mushrooms, may be called a 'strain'.

If one parental line carries allele 'p' at a particular locus, and the other parental line carries allele 'q', the F1 hybrid resulting from a mating of these two lines will carry both alleles, and the genotype can be represented as 'p/q' (or 'pq', or 'p+q'). Sequence-characterized markers are codominant and both alleles will be evident when an appropriate sequencing protocol is carried out on cellular DNA of the hybrid. The profile of line obtained from strain B12998 can therefore be used to identify hybrids comprising the line obtained from strain B12998 as a parent line, since such hybrids will comprise two sets of alleles, one of which sets will be from, and match that of, the line obtained from strain B12998. The match can be demonstrated by subtraction of the second allele from the genotype, leaving the allele contributed by the line obtained from B12998 evident at every locus. A refinement of this approach is possible with hybrids of *Agaricus bisporus* as a consequence of the heterokaryon (N+N) condition existing in hybrids. The two haploid nuclei can be physically isolated by various known techniques (e.g., protoplasting) into 'neohaplont' subcultures, and each may then be characterized independently. One of the two neohaplont nuclear genotypes from the F1 hybrid will be that of the line obtained from strain B12998, demonstrating its use in the mating and its presence in the hybrid.

A heterokaryotic selfed offspring of an F1 hybrid that itself has a 'p/q' genotype will in the example have a genotype of 'p/p', 'q/q', or 'p/q'. Two types of selfing lead to differing expectations about representation of alleles of a line obtained from strain B12998 and of the F1 hybrid in the next heterokaryotic generation. When two randomly obtained haploid offspring from the same F1 hybrid, derived from individual spores of different meiotic tetrads, are mated (i.e., in inter-tetrad selfing), representation of the line obtained from strain B12998 marker profile in each recombined haploid parental line and in each sib-mated heterokaryon will be 50% on average, and slightly more than 75% (to about 85%) of heteroallelism present in the F1 hybrid will on average be retained in the sib-mated heterokaryon (the expectation over 75% is due to the mating requirement for heteroallelism at the mating type locus (MAT) on Chromosome 1). Distinctively, in addition, *Agaricus bisporus* regularly undergoes a second, characteristic, spontaneous intra-tetrad form of selfing called intramixis, producing heterokaryotic postmeiotic spores carrying two different recombined haploid nuclei having complementary, heteroallelic MAT alleles. An offspring developing from any one of these spores is a postmeiotic self-mated heterokaryon with ca. 100% retention of the heteroallelism present in the single F1 parent around all 13 pairs of centromeres. In theory this value decreases to an average of 66.7% retention of F1 heteroallelism for distal markers unlinked to their centromeres; however empirical observations suggest higher rates of retention even for such distal markers. Transmission of the B12998-line marker profile in such selfed offspring may be incomplete by a small percentage (typically 0-10%) due to the effects of infrequent meiotic crossovers, while representing 50% on average of the resulting heterokaryotic genome. Both types of selfed offspring are considered to be Essentially Derived Varieties (EDVs) of the initial F1 hybrid, and the latter type comprises most (often 95-100%) of the genotype of the F1, and may express a very similar phenotype to that of the F1 hybrid.

Essentially Derived Varieties are most often derived directly from a single initial culture (e.g., strain); all such derivations produce EDVs. There is no universally accepted definition of an EDV; one example of a definition applicable to plant varieties is provided by the US Plant Variety Protection Act (revised edition, February 2006), incorporated herein by reference. The definition employed in this patent application is congruent with the term as it is widely understood. 'Essential derivation' methods of obtaining cultures which are by definition consequently EDVs of a single initial culture of *A. bisporus* include somatic selection, tissue culture selection, single spore germination, multiple spore germination, selfing, repeated mating back to the initial culture, mutagenesis, and transformation, to provide some examples of methods that are well known in the art. Repeated mating back to the initial culture to introgress a single trait into the genetic background of an initial variety or strain is called introgressive trait conversion, and produces an EDV of the initial strain. DNA-mediated transformation of *A. bisporus* has been reported by Velcko, A. J. Jr., Kerrigan, R. W., MacDonald, L. A., Wach, M. P., Schlagnhaufer, C., and Romaine, C. P. 2004, Expression of novel genes in *Agaricus bisporus* using an *Agrobacterium*-mediated transformation technique. Mush. Sci. 16: 591-597, and references therein, herein incorporated by reference. Transformation may introduce a single new gene or allele into the genome of an initial variety. For an EDV obtained by selfing from an initial strain, for example, B12998 and for the disclosed loci hereinabove, all of the markers present belong to a complete or partial subset of what is present in the fingerprint of the initial culture, which in this example is B12998. Said another way, for those loci, there is no marker present which is not also found in the fingerprint of the initial culture, in this example, strain B12998.

Therefore, in accordance with the above, one or more embodiments of this invention include a B12998-obtained-line progeny mushroom culture, culture part, mushroom, or mushroom part that is a first-generation (F1) heterokaryotic hybrid mushroom culture comprising two sets of alleles, wherein one set of alleles is the same as is present in a line obtained from strain B12998 at all of the known marker loci. A mushroom cell or hyphal element wherein one set of the alleles is the same as is present in a line obtained from strain B12998 at all of the known marker loci is also an embodiment of the invention. This mushroom cell or hyphal element may be a part of a culture, a commercial inoculum or 'spawn' product, a mushroom, or a part of a mushroom produced by mating a line obtained from strain B12998 with another mushroom culture. Further embodiments of this invention may include an Essentially Derived Variety of the F1 hybrid, produced by inter-tetrad or intra-tetrad selfing of the F1 hybrid, or by modification of the F1 culture, and more specifically by somatic selection, tissue culture selection, single spore germination, multiple spore germination, selfing, repeated mating back to the initial culture, mutagenesis, and transformation.

While many types of molecular markers are known, and can be used, all of these ultimately derive from the primary DNA sequence of the genome. The essential genotype of a line or strain is embodied in its genomic DNA sequence. The marker profiles presented in the tables including Table V below or in other genotype tables presented in a US application entitled "Mushroom Line B129998-s39 and Methods and Uses Therefor" filed concurrently herewith, represent a small selected excerpt of the known and deduced genome sequences of strain B12998, and of numerous other strains and lines of interest, usually at loci which are known to have differing sequences among other lines and strains, selected at widely spaced intervals spanning the entire nuclear genome. All heterokayons including hybrid strains will produce offspring lines having genotypes which are a haploid subset of the genotypes of their parent strain. Accordingly, the genotypes of offspring lines can be predicted within narrow ranges even when they are not completely known. Commercial sequencing providers and commercial technologies such as Illumina MiSeq, among others, may be used to obtain whole-genome sequences from total cellular DNA preparations. Other techniques for obtaining genotype profiles may also be used as appropriate.

Line B12998-s39 and its presence in cultures, culture parts, hybrids, mushrooms and mushroom parts can be identified through a molecular marker profile. This is equally true of other lines obtained from strain B12998 or from related strains. A mushroom culture cell or hyphal element having a marker profile shown in or predicted by Table V or the genotype tables presented in the concurrently filed US patent application entitled "Mushroom Line B129998-s39 and Methods and Uses Therefor" is an embodiment of the invention. Such a mushroom cell or hyphal element may be heterokaryotic.

Lines obtained from strain B12998 represent new base genetic lines into which a new locus or trait may be introgressed. Direct transformation and inbreeding represent two useful methods that can be applied to accomplish such an introgression. Introgression producing a trait conversion comprises the step of mating a line obtained from strain B12998 to a second strain, and then mating progeny of that mating with the line obtained from strain B12998, repetitively, until a derived variant of the B12998-line incorporating an introduced gene determining a novel trait is obtained. Strains and lines produced by this method may have, for example, in the range of 75, 80, 85, 90, 95, 96, 97, 98, 99, or 99.9% of the DNA of the B12998 strain or of a line obtained from B12998, and are therefore Essentially Derived from the B12998 strain or from a line obtained from strain B12998, and are an embodiment of the invention.

In order to demonstrate practice of the present invention, the line B12998-s39 (NRRL Accession No. 50899) was compared to other lines. B12998-s39 is a line selected from among 33 haploid progeny lines of a first generation in a hybrid pedigree initiated by Sylvan America, Inc. in 2011. This line, within a suitable heterokaryotic genetic background, dominantly confers a brown cap color trait upon heterokaryotic offspring; cap color is determined primarily by dominant and recessive alleles at the PPC-1 locus on Chromosome 8. Line B12998-s39 has the Mat-5 mating type genotype and behavioral phenotype. It also contributes to and supports several commercially desirable traits in hybrid offspring, including crop timing and productivity, and mushroom size, appearance and general retail appeal. While the other 32 obtained lines from strain B12998 are genotypically diverse, within the range of the parental genotype, a number of them are known to make similarly valuable contributions to their hybrid strain offspring. Because lines are haploid, they are individually incapable of producing a crop of mushrooms, and consequently no "B12998-line mushroom" is obtainable and no direct characterization of a crop or product phenotype is possible. Therefore most selection criteria applied to haploid lines including lines from B12998 are determined empirically by evaluating a series of matings which share a common parent. In effect, this 'combining ability', i.e., the ability to mate successfully and produce a high proportion of interesting and useful novel hybrids in strain development programs, is applied using qualitative, quantitative, objective and subjective criteria. Line B12998-s39 is among the top-ranked haploid lines discovered from among its cohort of sibling lines. No other hybrid, prior to creation of hybrids using lines from B12998, had been observed previously to have had a commercially acceptable likelihood of combining to create the particular combination of desirable traits (including general appearance and product quality, productivity and accelerated cropping, plus a particular novel incompatibility phenotype) seen among hybrids incorporating line B12998-s39, and also seen among less completely characterized hybrids incorporating other lines obtained from strain B12998, as described in Sylvan America, Inc.'s corresponding patent application filed the same day and entitled "Hybrid Mushroom Strain B14528 and Descendants Thereof", herein incorporated by reference. No BW lines have ever previously been observed to produce the particular combinations of desirable traits observed among hybrids incorporating lines obtained from B12998.

A single mushroom hybrid results from the mating of two haploid, homoallelic lines, each of which has a genotype that complements the genotype of the other. The hybrid progeny of the first generation is designated F1. F1 hybrids may be useful as new commercial varieties for mushroom production, or as starting material for the production of inbred offspring and/or EDVs, or as parents of the next generation of haploid lines for producing subsequent hybrid strains.

Lines obtained from hybrid strain B12998, lines obtained from hybrids strains having strain BP-1 as one parent and either an SW strain, an OW strain, an HW strain, or an experimental BW strain as a second parent, and lines obtained from hybrids having B12998 as at least one parent, may be used to produce hybrid mushroom cultures. One such embodiment is the method of mating homokaryotic line obtained from one of the hybrid strains described in this paragraph hereinabove with another homokaryotic mushroom line, to produce a first generation F1 hybrid culture. The first generation culture, culture part, mushroom, and mushroom part produced by this method is an embodiment of the invention. The first generation F1 culture will comprise a complete set of the alleles of the two homokaryotic lines that were mated to produce the hybrid strain. The strain developer can use either strain development records or molecular methods to identify a particular F1 hybrid culture produced using a line described in this paragraph hereinabove. Further, the strain developer may also produce F1 hybrids using lines which are transgenic or introgressive trait conversions (narrow modifications') of a line described in this paragraph hereinabove. Another embodiment is the method of mating a line described in this paragraph hereinabove, or a narrowly modified version of that line, with a different, heterokaryotic culture of *Agaricus bisporus*. This latter method is less efficient than mating using two homokaryotic lines, but can also result in the production of novel hybrid cultures.

The development of a mushroom hybrid in a typical mushroom strain development program involves many or all of the following steps: (1) the obtaining of strains or stocks from various germplasm pools of the mushroom species for initial matings; (2) matings between pairs of pure cultures on sterile microbiological growth media such as potato dextrose agar (PDA); (3) the obtaining and use of promising hybrid strains from matings to produce subsequent generations of homokaryotic progeny lines, such as lines obtained from strain B12998, which are individually uniform; (4) the use of those lines in matings with other lines or strains to produce a subsequent hybrid generation; (5) repetition of steps (2-4) as needed; (6) obtaining of pre-commercial hybrid strains and the use of essential derivation techniques such as selfing to produce a final commercial strain. In one embodiment, the repetition of steps (2-4) may be performed up to 5 times. In various other embodiments, steps (2) to (4) may be repeated anywhere from 0 up to 1, 2, 3, 4, 5, 6, 7, 8, 9 or 10 times. The homokaryotic lines are not reproductively competent ('fertile'). Fertility, the ability to produce a crop of mushrooms, is restored in complementary matings with other haploid, or less commonly, heterokaryotic strains. An important consequence of the homoallelism and homogeneity of the homokaryotic line is that the hybrid between a defined pair of homokaryotic lines may be recreated indefinitely as long as the homokaryotic lines are preserved and/or propagated. In a mating attempt between a homokaryotic line and a heterokaryon, in the absence of somatic recombination, either or both of only two possible defined novel heterokaryotic genotypes may be obtained, each of which will comprise the homokaryotic line.

Using lines obtained from strain B12998, or from related strains, specific application with repetition of the steps described above can produce any pedigree structure from any arrangement of stocks, lines and hybrids within that structure. A hybrid of the F1, F2, F3, F4, F5, F6, F7, F8, F9, F10 or any subsequent hybrid generation can be produced from lines obtained from strain B12998 using steps 1-6 described above.

Although the invention has been described in terms of particular embodiments in this application, one of ordinary skill in the art, in light of the teachings herein, can generate additional embodiments and modifications without departing from the spirit of, or exceeding the scope of, the claimed invention. Accordingly, it is understood that the descriptions herein are proffered only to facilitate comprehension of the invention and should not be construed to limit the scope thereof.

What is claimed is:

1. A hybrid BW-type mushroom strain culture having a strain belonging to a derived lineage group which consists of an initial strain BP-1, a culture of which is available from ATCC under Accession No. PTA-6903, and strains derived entirely from the initial strain BP-1 and having 90 to 100% of the genotype of the initial strain BP-1, as a first parent, and a strain selected from among the group of strain types consisting of: strains belonging to a derived lineage group comprised of strains derived entirely from Off White-type strains (OW-type strains) having a genetic marker profile incorporating only markers present in a genetic marker profile of Somycel 76, a culture of which is available from NRRL under Accession No. 50903, strains belonging to a derived linage group comprised of strains derived entirely from Smooth White-type strains (SW-type strains) having a genetic marker profile incorporating only markers present in a genetic marker profile of Somycel 53, a culture of which is available from NRRL under Accession No. 50904, and a derived lineage group comprised of Hybrid White-type hybrid strains (HW-type hybrid strains) consisting of an initial strain U1, a culture of which is available from ATCC under Accession No. 62462, an initial strain B7970, a culture of which is available from ATCC under Accession No. PTA-4887, an initial strain J9277, a culture of which is available from ATCC under Accession No. PTA-6692, and an initial strain J11500, a culture of which is available from NRRL under Accession No. 50895, and strains derived entirely from any of initial strains U1, B7970, J9277 and J11500 and having 90 to 100% of the genotype of one of the initial strains U1, B7970, J9277 and J11500, as a second parent, wherein the hybrid BW-type mushroom strain culture results from the mating of the first and second parents.

2. A part of the hybrid BW-type mushroom strain culture of claim 1 selected from the group consisting of hyphae, mushrooms, spores, cells, and protoplasts.

3. A product incorporating the hybrid BW-type mushroom strain culture of claim 1, the product selected from the group consisting of mycelium, spawn, inoculum, casing inoculum, fresh mushrooms, processed mushrooms, mushroom extracts and fractions, mushroom pieces, and colonized substrates including grain, compost, and friable particulate matter.

4. The method of obtaining offspring of the hybrid BW-type mushroom strain culture of claim 1, comprising the steps of: obtaining a mushroom from said hybrid BW-type mushroom strain culture, obtaining spores from said mushroom, germinating said spores, transferring cultures from germinating spores to new growth media.

5. Offspring obtained by the method of claim 4.

6. The hybrid BW-type mushroom strain culture of claim 1 having acceptable agronomic characteristics.

7. A hybrid mushroom strain culture designated B12998, a culture of which has been deposited under NRRL Accession No. 50902.

8. A homokaryon obtained from the hybrid mushroom strain culture of claim 7.

9. A culture of the strain developed entirely from the hybrid mushroom strain culture of claim 7, wherein at least 90% of its genome or genotype is present in the genome or genotype of the initial culture of strain B12998, wherein a culture of the initial strain B12998 has been deposited under NRRL Accession No. 50902.

10. A homokaryon obtained from the culture of claim 9.

11. The homokaryon of claim 8 having acceptable agronomic characteristics.

12. A heterokaryon obtained from the hybrid mushroom strain culture of claim 7.

13. A part of a BW-type hybrid mushroom strain culture incorporating the homokaryon of claim 8 selected from the group consisting of hyphae, mushrooms, cells, and protoplasts.

14. A product incorporating the homokaryon of claim 8, the product selected from the group consisting of mycelium, spawn, inoculum, casing inoculum, fresh mushrooms, processed mushrooms, mushroom extracts and fractions, mushroom pieces, and colonized substrates including grain, compost, and friable particulate matter.

15. A method of producing a hybrid BW-type mushroom strain culture having a strain belonging to a derived lineage group which consists of an initial strain BP-1, a culture of which is available from ATCC under Accession No. PTA-6903, and strains derived entirely from the initial strain BP-1 and having 90 to 100% of the genotype of the initial strain BP-1, as a first parent and a strain selected from among the group of strain types consisting of: strains belonging to a derived lineage group comprised of strains derived entirely from Off White-type strains (OW-type strains) having a genetic marker profile incorporating only markers present in a genetic marker profile of Somycel 76, a culture of which is available from NRRL under Accession No. 50903, strains belonging to a derived linage group comprised of strains derived entirely from Smooth White-type strains (SW-type strains) having a genetic marker profile incorporating only markers present in a genetic marker profile of Somycel 53, a culture of which is available from NRRL under Accession No. 50904, and a derived lineage group comprised of Hybrid White-type hybrid strains (HW-type hybrid strains) consisting of an initial strain U1, a culture of which is available from ATCC under Accession No. 62462, an initial strain B7970, a culture of which is available from ATCC under Accesion No. PTA-4887, an initial strain J9277, a culture of which is available from ATCC under Accession No. PTA-6692, and an initial strain J11500, a culture of which is available from NRRL under Accession No. 50895, and, strains derived entirely from any of initial strains U1, B7970, J9277 and J11500 and having 90 to 100% of the genotype of one of the initial strains U1, B7970, J9277 and J11500, as a second parent, comprising the steps of: mating a culture from the first parent, including homokaryotic offspring line cultures, with a culture from the second parent, including homokaryotic offspring line cultures, to obtain a hybrid BW-type culture; isolating the hybrid BW-type culture in pure form by transferring it to fresh nutrient growth medium.

\* \* \* \* \*